United States Patent [19]

Steinhaus et al.

[11] Patent Number: 5,139,028
[45] Date of Patent: Aug. 18, 1992

[54] HEART REJECTION MONITORING APPARATUS AND METHOD

[75] Inventors: Bruce M. Steinhaus; Fred I. Vance, both of Parker, Colo.; Anne Curtis, Gainesville, Fla.; Ken Koestner, Englewood, Colo.

[73] Assignee: Telectronics Pacing Systems, Inc., Englewood, Colo.

[21] Appl. No.: 604,901

[22] Filed: Oct. 26, 1990

[51] Int. Cl.$^5$ .............................................. A61N 1/08
[52] U.S. Cl. .................................... 128/697; 128/696
[58] Field of Search ......................... 128/695, 696, 697

[56] References Cited

U.S. PATENT DOCUMENTS

| 4,531,936 | 7/1985 | Gordon | 604/49 |
| 4,692,719 | 9/1987 | Whigham | 332/11 D |
| 4,821,724 | 4/1989 | Whigham et al. | 128/419 P |

OTHER PUBLICATIONS

A. Keren et al., "Heart Transplant Rejection Monitored By Signal-Averaged Electrocardiography in Patients Receiving Cyclosporine," *Circulation*, vol. 70 (Suppl I), pp. I-124 through I-128 (Sep. 1984).

H. Warnecke et al., "Noninvasive Monitoring of Cardiac Allograft Rejection By Intramyocardial Electrogram Recordings," *Circulation*, vol. 74 (Suppl. III), pp. III-72 through III-76 (Nov. 1986).

R. Haberl et al., "Frequency Analysis of the Surface Electrocardiogram for Recognition of Acute Rejection After Orthotopic Cardiac Transplantation in Man," *Circulation*, vol. 76, No. 1, pp. 101-108 (Jul. 1987).

A. A. Grace et al., "Assessment of Intracardiac T Wave Amplitude Measurement in Predicting Cardiac Allograft Rejection," *PACE*, vol. 13, pp. 542, Abstract No. 180 (Apr. 1990).

*Primary Examiner*—William E. Kamm
*Assistant Examiner*—Scott M. Getzow
*Attorney, Agent, or Firm*—Gottlieb, Rackman & Reisman

[57] ABSTRACT

An implantable cardiac allograft rejection monitoring apparatus and method for measuring stimulated intracardiac electrogram potentials, performing processing and time based analysis of changes in the potential, and deriving from the time history of the analyzed signals allograft rejection control parameters. The apparatus communicates the allograft rejection control parameters to an external communicating device and may use the parameters to control the output of an implanted drug infusion pump.

24 Claims, 8 Drawing Sheets

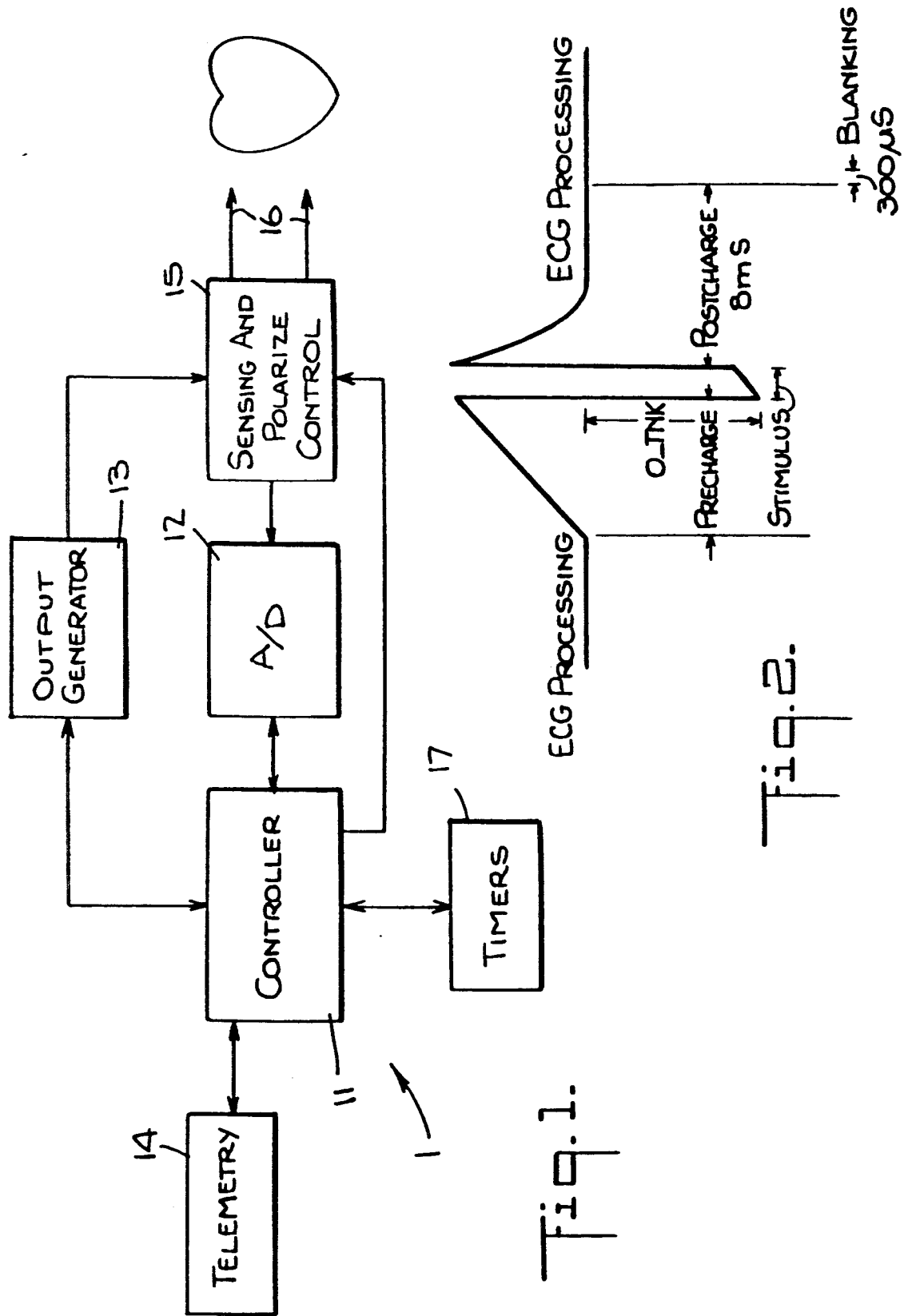

HEART REJECTION MONITORING APPARATUS AND METHOD

BACKGROUND OF THE INVENTION

This invention relates to an apparatus and method for monitoring the cardiac function of heart transplant patients for the purpose of detecting cardiac allograft rejection, and more particularly to an apparatus and method for detecting cardiac allograft rejection and responding to such detection by providing a warning signal to the patient or by controlling the output of an implanted infusion pump adapted to administer antirejection drugs.

Cardiac transplantation is an accepted therapy for end stage cardiac disease. After transplantation, cardiac allograft rejection by the patient's immune system is a serious and life-long problem requiring intensive medical therapy and close follow-up. In the early years of cardiac transplantation, immunosuppressing drugs such as azathioprine and steroids were used to treat heart rejection problems. To determine when to administer these drugs and the proper dosage, physicians would perform periodic endomyocardial biopsy operations.

Typically a cardiac transplant patient undergoes an endomyocardial biopsy once per week immediately after transplantation and less frequently thereafter. An average patient will have twelve biopsies in the first year after transplantation. The biopsy schedule increases if the physician suspects rejection.

To perform a cardiac biopsy operation, the physician introduces a large catheter into the body through the femoral or jugular vein. The operation is uncomfortable and inconvenient for the patient, potential complications are infection, arrhythmias, heart block, and cardiac perforation. Biopsy is an invasive operation; therefore some recovery time must transpire between operations. In the interim period, rejection may begin or worsen without detection. In addition, the physician must presume, possibly incorrectly, that a limited sample of tissue reflects the histology of the heart as a whole.

An alternative method to monitor and detect rejection is highly desirable to avoid the need for repeated invasive endomyocardial biopsy procedures. The first attempts to develop such an alternative employed standard body surface electrocardiogram sensing techniques wherein physicians would analyze the cardiac electrical signals of natural (not stimulated) heartbeats. A gradual decrease in the electrocardiogram amplitude over a period of a few days showed some correlation with heart rejection. Unfortunately, this manner of diagnosis has proven inaccurate in a high percentage of studies, often giving widely variable results from patient to patient and even from one study to the next in the same patient. Further reducing the diagnostic value of body surface electrocardiogram analysis is the fact that the amplitude reduction appears only late in the course of rejection, if it even appears in a diagnostic manner.

A report by A. Keren et al., entitled "Heart Rejection Transplant Monitoring by Signal-averaged Electrocardiography in Patients Receiving Cyclosporine", CIRCULATION, Vol. 70, pages 1-124 (1984), indicates that some improvement in the diagnostic utility of body surface electrocardiogram analysis has been achieved by using signal-averaging techniques. But even these techniques have proven inadequate for detecting rejection shortly after the transplant operation or for detecting mild rejection some time after the transplant operation. Other researchers have improved body surface sensing and analysis results by performing frequency analysis of the electrocardiogram. See, for example, the report by R. Haberl et al., entitled "Frequency Analysis of the Surface Electrogram for Recognition of Acute Rejection After Orthotopic Cardiac Transplantation in Man", CIRCULATION, Vol. 76, page 101 (1987). Frequency analysis shows that changes in spectral morphology, rather than QRS amplitude, offers improved correlation with rejection. To date, none of the body surface electrogram sensing techniques has shown sufficient sensitivity and specificity to replace the biopsy for the detection of rejection.

Since the time of the first application of body surface electrocardiogram sensing techniques to the problem of rejection prediction, cyclosporine became available for usage as an immunosuppressive agent. Cyclosporine led to the improved survival among transplant recipients as well as an increase in the use of transplantation as a treatment for severe cardiac disease. Immunosuppression treatment using cyclosporine is an improvement over treatment with azathioprine and steroids because it is associated with less myocardiac edema. Unfortunately, reduced myocardiac edema lessens the signs of rejection on the standard external electrocardiogram. Because cyclosporine treatment has further diminished the diagnostic efficacy of external electrocardiograms, endomyocardial biopsy is now the only reliable method for detecting rejection in the transplanted heart.

The intrinsic intracardiac electrogram, measured from leads implanted within the heart, is another type of cardiac electrical signal previously evaluated to detect allograft rejection. See, for example, the report by H. Warnecke et al., entitled "Noninvasive Monitoring of Cardiac Allograph Rejection by Intramyocardial Electrogram Recordings", CIRCULATION, Vol. 74, page III-72 (1986). Although intracardiac electrogram monitoring requires the implantation of a sensing electrode and a signal detecting and transmitting device, rendering the procedure technically invasive, following implantation the device sends signals to an external communicating device in a non-invasive manner.

SUMMARY OF THE INVENTION

Briefly stated, and in accordance with one aspect of the present invention, there is provided an implanted device for noninvasively detecting cardiac allograft rejection by periodically measuring, analyzing, and tracking gradual changes of a cardiac depolarization potential, the signal waveform of the intramyocardial electrogram, in response to a generated stimulating pulse.

In accordance with another aspect of the present invention, there is provided a method of monitoring cardiac allograft rejection from leads implanted in a patient's heart by periodically measuring, analyzing and tracking gradual changes of a cardiac depolarization potential in response to a generated stimulating pulse.

The device and method allow a reduction in the number and frequency of cardiac biopsy operations performed on heart transplant patients. The chronically implanted apparatus and method disclosed herein automatically (requiring no oversight by a health care professional) performs all aspects of rejection monitoring including sampling, data processing, analysis, and decision-making. The device conveniently monitors rejection as often as desired, even continuously, without requiring the repeated surgical invasions necessary using biopsy methods. Results of the monitoring are accessible to an external device upon demand using telemetric communication. Existing techniques for monitoring rejection, including endomyocardial biopsy, are limited because rejection is only determined at discrete points in time with the intermediate patient status largely unknown.

The automaticity of the implanted device extends the usefulness of the rejection monitoring technique in a number of ways. Rejection monitoring becomes much more convenient and inexpensive, allowing continuous monitoring of the patient without the requirement of additional personnel or equipment. The test for allograft rejection becomes a simple, quick, noninvasive interrogation by an external telemetric device at the convenience of the physician. Since the implanted device stores a time record of rejection parameter measurements, a physician has more information to form a basis for diagnostic and therapeutic decisions. Automaticity also allows the device to independently control the function of therapeutic devices such as implanted drug delivery mechanisms and to improve the sensitivity of the device to the patient's drug dosage requirements. A controllable, implanted infusion pump, for example, the one described in U.S. Pat. No. 4,531,936, entitled "Device and Method for the Selective Delivery of Drugs to the Myocardium", may be employed as the drug delivery mechanism. Thus, titration of the patient's medications to suppress the immune system can be based on the waveform analysis and can be regulated in a closed-loop feedback manner.

One advantage of intracardiac electrogram analysis methods over prior art body surface electrogram measurement techniques is that it provides a greatly improved signal for diagnosis of allograft rejection. Signals recorded from electrodes within the heart are not subject to the attenuation inherent with body surface electrode recording in which the signals are measured some distance from the source of the signal. The poor signal to noise ratio of signals generated using body surface electrocardiogram sensing methods is a factor leading to their inadequate reliability in detecting rejection. This is because of the susceptibility of such signals to interference (muscle noise, power line and high frequency communication equipment interference, and baseline drift from respiration), contact problems, and electrocardiogram waveform artifacts. Also, externally attached electrodes are subject to motion artifacts from positional changes and the relative displacement between the skin and the electrodes. In contrast, the implanted device measures a high quality signal, enabling the reliability of its sensing of allograft rejection to approach that of biopsy analysis and providing an improved predictor of cardiac allograft rejection.

Inconvenience of measurement is a further disadvantage of body surface measurements techniques as compared to the implanted device. External electrodes require special skin preparation and care to prevent signal corruption from dislodgement.

Some understanding of the electrical properties of the heart is necessary to better acknowledge the improvements in diagnostic capabilities inherent in the present invention. Intracardiac electrograms are recordings of the electrical potentials measured from electrodes implanted within the heart. The intrinsic electrocardiogram arises from the natural (not stimulated) activity of the heart and typically has a biphasic waveform during depolarization, the form of which depends on the location of the sensing electrode and the dynamics of natural polarization. In contrast, the electrical response of the heart to stimulation, measured at the site of the stimulus, arising from a suprathreshold pulse generated by the device is commonly a monophasic negative waveform during depolarization. Both signals are similar in that they arise from the electrical currents generated by the cardiac membrane but they differ in both the spatiotemporal distribution of the currents and in the information content of the waveforms. The form of both signals varies from patient to patient depending on the location of the implanted leads and the electrophysiological condition of the heart. Nonetheless, the form of the stimulated cardiac depolarization potential is much less variable than the intrinsic potential because the location of the stimulus is always the same in relation to the electrodes.

In the case of the intrinsic polarization signal, the time waveform may vary greatly from implant to implant because the spreading polarization wave of the heart may proceed from different directions. Consequently, the intrinsic waveform may monophasic, biphasic or even multiphasic in form. The relative durations of each phase of the intrinsic waveform may be greatly variable and the direction of polarization may be reversed from one implant to another. In addition, the amplitudes of intrinsic signals are dependent on the location of the electrodes. For example, the active and indifferent electrodes may be situated such that the spread of polarization hits each electrode simultaneously, resulting in no detectable polarization amplitude. In contrast, the stimulated waveform will always have a monophasic negative form since the source of the stimulating signal, the active electrode, will always be situated in the same spatial relationship to the sensing electrode since the two electrodes are the same.

In addition to the variability of the intrinsic waveform morphology from one implant to another, the intrinsic waveform will vary more from one cardiac cycle to the next than will the stimulated polarization signal. The intrinsic signal changes because of the natural variability in the electrical conduction pattern inherent in biological systems. The stimulated polarization signal will not normally differ greatly from one cycle to the next because the source of the stimulation always remains the same relative to the sensing electrode.

Electrophysiological research and computer modelling of intrinsic and stimulated polarization waveforms indicates that the magnitude of the amplitude and integrated area of the depolarization waveform are reduced in the presence of cardiac allograft rejection. When rejection takes place, the depolarization waveform does not decay as rapidly. The probable mechanism for these waveform changes stems from the fact that cardiac allograft rejection is characterized by an increased cell to cell coupling resistance, leading to a decrease in the amplitude of both the intrinsic and stimulated response. During tissue rejection of the donor heart, histological studies have shown increased infiltration of fatty tissue throughout the muscle and often accumulation of collagenous tissue areas within the heart. The electrical consequence of this is to disrupt the cell to cell connections. An electrical model of this would be to increase the cell to cell coupling resistance, causing both intrinsic and stimulated electrogram depolarization potentials to generally decrease in amplitude and increase in width. In accordance with the teachings of our invention, the best standard of measurement, or metric, of cardiac allograft rejection is the ratio of depolarization signal amplitude to width, as measured from a stimulated potential waveform.

Accordingly, the present allograft rejection detection device periodically measures stimulated cardiac depolarization potential signals over time and analyzes this information to detect gradual changes in a metric which correlates well with rejection. The preferred embodiment of the invention measures polarization wave amplitude, width and area for both depolarization samples and combined depolarization and repolarization samples.

No prior art intrinsic intracardiac electrogram techniques are known which perform the automatic analysis and decision-making functions of the present invention. In known prior art techniques, a physician specializing in electrophysiology or cardiology performs intrinsic intracardiac electrogram analysis by means of visual inspection. These prior art techniques do not include automatic analysis because of the complexity of the intrinsic electrocardiogram waveform. The simple, monophasic waveform of the stimulated cardiac depolarization potential signal of the present invention promotes automaticity because the device is not required to analyze a complex waveform having multiple phases but rather can simply search for a negative maximum magnitude signal and a zero-crossing change in polarity from negative to positive phase.

In addition, the analysis of stimulated waveforms provides for greater reliability because the signal is more uniform on a cardiac cycle to cycle basis. The natural variability of the intrinsic polarization waveform can lead to false positive and false negative rejection decisions. Although the stimulated waveform is subject to long-term variability, mainly caused by changes in impedance of the leads, the preferred embodiment of the invention deals with slow changes appropriately to avoid incorrect test results.

The present invention offers further improvement over the prior art intrinsic polarization measurement techniques by providing for less complex signal averaging techniques. Reliable biological signal analysis schemes generally require averaging on a cycle by cycle basis to reduce the influence of normal variability on the test result. This necessitates the alignment in time of the samples for each cardiac cycle. The time alignment procedure is complex, requires a high degree of computation, and is subject to error. Time alignment is not required for stimulated depolarization signals because the stimulus generation triggers and synchronizes the sample timing.

One objective of the preferred embodiment of the invention is to maximize the reliability of the allograft rejection decision-making process. Consequently, the device generates the stimulus and senses the signal in a manner which optimizes the diagnostic features of the stimulated polarization waveform. The device automatically adjusts sensing sensitivity to provide the largest signal without saturation. In addition, the system adjusts the stimulation amplitude to the smallest level which will generally successfully stimulate the heart and monitors the heart response to guarantee that the heart is successfully stimulated before performing the diagnostic measurement. The automatic stimulation amplitude function insures that the device compares similar signals over time. The device also improves diagnostic reliability by performing automatic artifact reduction to minimize the size of the stimulation polarization artifact. Although the stimulated cardiac depolarization potential analysis methods of the present invention improve the reliability of allograft rejection detection as compared to the prior art intrinsic intracardiac electrogram techniques even without these automatic functions, the improvements fit efficiently into the framework of a stimulated signal sensing and analysis system.

The ability to automatically reduce stimulation polarization artifacts is necessary in a system which analyzes the depolarization waveform stimulated by a pulse because, in addition to generating a cardiac response, an electrical stimulus gives rise to a form of noise called the stimulation polarization artifact. When a device generates an electrical stimulus within the heart, it creates electrical charges which are stored in the body tissues. The stimulation polarization artifact is the signal arising from the dissipation of these stored charges. The amplitude of the stimulation polarization artifact is normally so much greater than that of signals arising from a natural heartbeat or the stimulated response that it is usually futile to sense these diagnostic signals until the stimulation polarization artifact charges dissipate. This is especially true when, as in the case of the preferred embodiment of the present invention, the device uses the same electrode for stimulating and sensing.

To rapidly dissipate these charges and minimize the stimulation polarization artifact at the pacing electrode, the device generates stimulating pulses using a technique known as charge balancing. The procedure and circuit for performing charge balancing is disclosed in U.S. Pat. No. 4,821,724, entitled "Pacing Pulse Compensation", which issued on Apr. 18, 1989, and refers to the method as active recharge. This patent is assigned to the assignee of the present application and its disclosure is incorporated herein by reference. In this procedure, the device generates a triphasic stimulus, with the first and third phases being of one polarity and the second being of the opposite polarity. The amplitudes of the first and second phases are substantially proportional to each other. The third phase drives a current through the stimulating electrode until the voltage equals the starting quiescent voltage.

The charge balancing technique, also called the stimulation polarization artifact reduction technique, as performed by the preferred embodiment of the present invention, requires circuitry for sensing cardiac electrical activity including natural polarizations, stimulated potentials and artifacts. This sensing circuitry is disclosed in U.S. Pat. No. 4,692,719, entitled "Combined Pacemaker Delta Modulator and Bandpass Filter", which issued on Sep. 8, 1987. This patent is also assigned to the assignee of the present application and its disclosure is incorporated herein by reference.

The ability to reduce the stimulation polarization artifact in the present invention provides the capability of measuring the stimulus depolarization signal which, to our knowledge, is superior to all other signals in terms of reliability and efficient implementation for diagnosing allograft rejection. One inferior signal for such diagnosing is the repolarization signal, or T-wave, following a stimulated depolarization. See, for example, the abstract by A. Grace et al., entitled "Assessment of Intracardiac T Wave Amplitude Measurement in Predicting Cardiac Allograft Rejection", PACE, Vol. 13, page 542 (1990). The depolarization signal generally has a greater amplitude than the repolarization signal, providing a greater signal to noise ratio for diagnosis since the noise levels in each case are comparable. In addition the morphology of the repolarization waveform is more variable than the depolarization signal in a particular implant and on a cycle by cycle basis because the repolarization morphology and polarity depends on the spatiotemporal conduction characteristics of the surrounding tissue.

The above objects and advantages, in addition to others that will appear in the detailed description of the invention, will be more clearly understood by reference to the accompanying drawings, the following description, and the appended claims.

BRIEF DESCRIPTION OF THE DRAWINGS

FIG. 1 is a block diagram of an illustrative embodiment of the invention in the form of an allograft rejection monitoring apparatus;

FIG. 2 depicts the form of the triphasic stimulation pulse generated by an output generator block of FIG. 1;

FIG. 8 is a flow chart illustrating the operational steps of the allograft rejection control parameter derivation performed by the illustrative embodiment of the invention;

DETAILED DESCRIPTION

Figure 3:
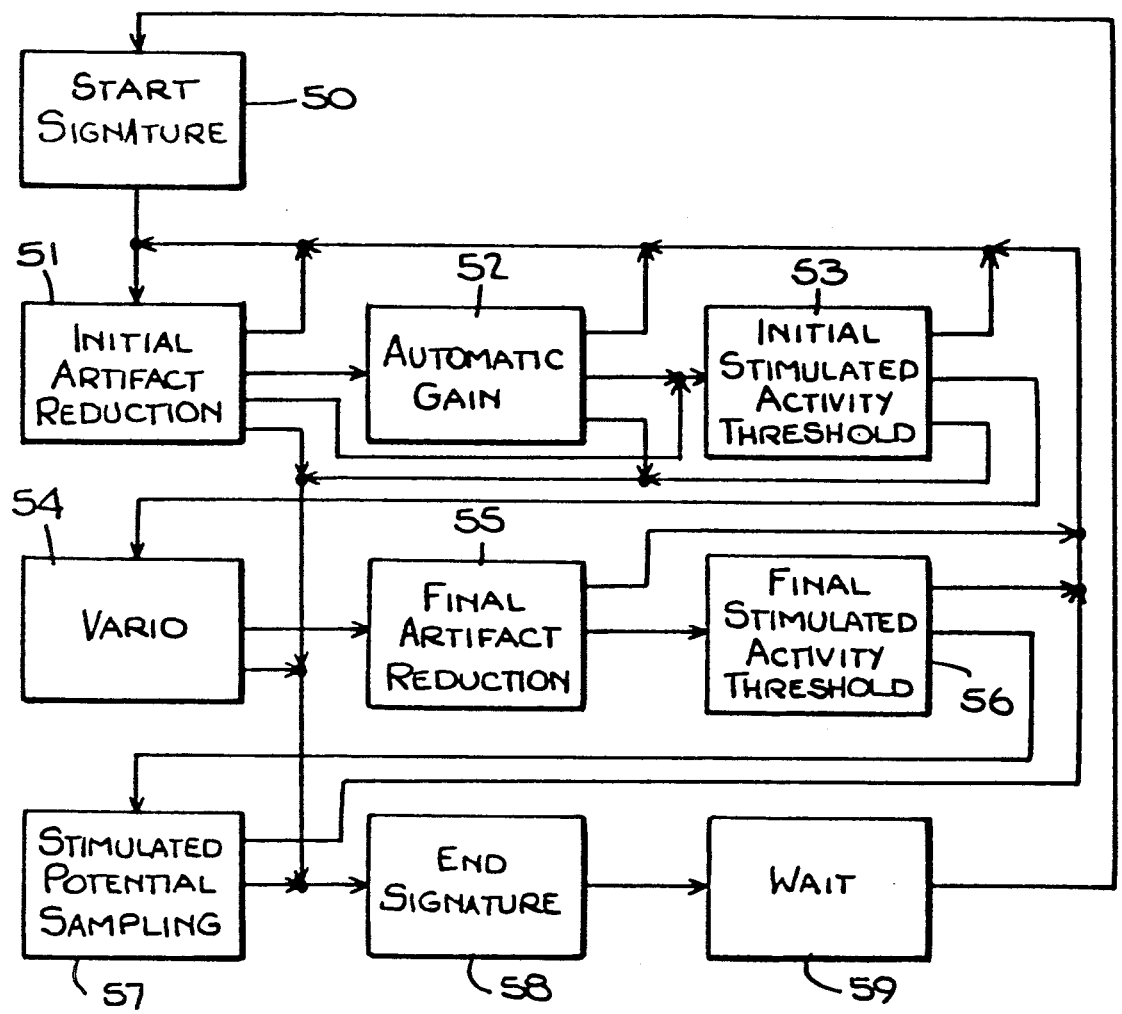
FIG. 3 is a flow chart illustrating the operational steps of stimulation polarization artifact reduction, automatic sensitivity control, and automatic stimulus output determination performed by the illustrative embodiment of the invention.

FIG. 1 illustrates in a highly symbolic block-diagram form an implanted apparatus or device, shown generally at 1, for predicting heart transplant rejection. The fundamental requirements for such a device include the capabilities of generating and delivering electrical stimulations in various amplitudes and forms. The device must then sense the stimulated response, the response of cardiac tissue to the electrical stimulus, and convert the stimulated response signal into a proper form for analysis. The device then analyzes the signal and stores the resulting data in memory. The device transmits the stored data to an external device upon command.

A controller 11 controls all of the other blocks of FIG. 1. In particular, the controller determines the amplitude and morphology of the stimulating pulse and also sets the timing of pulse delivery. The controller sets the pulse delivery parameters for the purpose of charge balancing the stimulus output. The controller also governs the timing and number of intracardiac electrogram samples in addition to determining and executing any signal filtering required for signal analysis. As the controller performs signal sampling, it carries out the analysis necessary for the diagnostic purposes of the device, as described below.

A telemetry block 14 is conventional in modern implanted cardiac pacemakers and defibrillators. It allows both adjustment of the data acquisition parameters from an external programmer and the transmission of information from the implanted apparatus to the external device. This information includes accumulated data and a signal representative of the instantaneous sensed intracardiac electrogram. Present-day sophisticated telemetry circuits allow for the interrogation of stored diagnostic data and the derivation of real-time operational data.

The apparatus uses a form of delta modulation to produce a digital signal for analysis by controller 11. An analog-to-digital block 12 is provided with a signal called ANGL_CMP from a sensing and polarization controller 15. The ANGL_CMP signal is a two level waveform representing the sensed signal as a sequence of bits indicating the time history of increases and decreases in the signal amplitude. The analog-to-digital block 12 converts the bit sequence into a form which the controller can read to perform the functions of sensing and intracardiac electrogram acquisition. The output signal of the analog-to-digital block 12 tracks the input signal in the sense that the output represents a 1 value when the input is increasing and a 0 value when the input is decreasing.

The controller 11 has a direct connection for controlling the sensing and polarization controller 15. The sensing and polarization controller has control circuits for performing data acquisition and pulse generation. To control sensing sensitivity, the controller 11 writes commands into the sensing and polarization controller 15 to adjust an 8-bit register which, in turn, sets each of eight switches within a resistor network circuit to an open or closed condition.

Control words written from the controller 11 to the sensing and polarization controller 15 determine the configuration of its sensing and stimulation circuits. The device delivers a negative polarity stimulus through that conductor of the lead 16 which has an electrical connection to the tip electrode of the lead. Other electrode connections of apparatus 1 are its case (the electrical connection is with the physical case of the device) and the ring electrode of lead 16. The device may connect in either a unipolar or bipolar fashion to leads 16. When connected in a unipolar mode, the active electrode is at the lead tip, which is in contact with the cardiac tissue to be stimulated, and the indifferent electrode is the case of the implanted device. When connected in a bipolar mode, the indifferent electrode can be either the case or the ring electrode, which is an annular electrode on the lead a short distance from the tip electrode. A command code written by the controller 11 determines the settings of switches to determine which electrode is active and which is indifferent during stimulation as well as sensing. The code may specify a different switch setting during stimulation as compared to sensing. Switch settings determine the operative configuration of the device: bipolar, unipolar tip-case or unipolar ring-case. Unipolar signals, arising from cardiac potentials accumulated over a larger surface of the ventricle, generally contain more information than bipolar signals, providing a more reliable diagnostic result. On the other hand, bipolar signals offer better rejection of noise, including muscle and motion artifacts, and provide the most detailed signal description of the electrophysiological state from a localized region of the ventricle. Control bytes written by the controller 11 to the sensing and polarization controller 15 determine the setting of other switches to accomplish the tasks of various modes of stimulation and sensor measurement acquisition. These switch settings are described in detail in the aforesaid U.S. Pat. No. 4,821,724.

An output generator 13, in response to control bytes written by the controller 11, prepares for stimulation by storing electrical charge on capacitors and delivers the stimulating pulses, as described in said U.S. Pat. No. 4,821,724. Control bytes written to the output generator by the controller 11 determine the amplitudes, polarities and durations of the phases of the pacing stimulus pulses. FIG. 2 illustrates the four periods or zones of the pacing stimulus pulse: precharge, stimulus, postcharge, and blanking. It is to be understood that the waveform of FIG. 2 is not drawn to scale. The controller 11 determines the duration of the precharge period, the postcharge interval duration (typically about 8 milliseconds), and the width of the negative portion of the stimulus pulse (usually in the range of 0.1 to 1.0 and commonly 0.5 milliseconds). After the stimulus pulse, the output generator times a blanking interval of about 300 microseconds to allow the circuit to settle after stimulation. The waveform of FIG. 2 represents the potential between the conductors of the lead 16 of FIG. 1. One objective of the invention is for the controller to set the amplitudes and durations for these four periods in a manner to minimize the stimulation polarization artifact at the tip or pacing electrode, providing reliable sensing of the heart's stimulated potential resulting from a generated pulse.

For a particular implanted lead, the controller 11 can adjust the precharge period to minimize the after-potential at the pacing electrode following the 8 millisecond postcharge duration. The precharge duration ranges from 0 to about 4 milliseconds. A typical precharge period is about 3 milliseconds when using an 8 millisecond postcharge interval. The device uses an arbitrarily selected postcharge duration of 8 milliseconds, since this is sufficiently short to permit sensing of the stimulated potential.

The controller 11 writes set-up and duration information to a timer 17. The timer 17 responds to this information by generating wake-up signals to the controller after the designated time expires. The controller uses timer wake-ups to govern the timing of cardiac cycles as well as to time short-term intervals for miscellaneous operations including the setting of timing for intracardiac electrogram sampling. In addition, the controller uses timer wake-up signals to control a real-time clock function for determining the length of time since manufacture of the device and for initiating long-term housekeeping functions. One such function is the control of heart rejection monitoring timing. Heart rejection monitoring requires the measurement and analysis of stimulated potential signals several times per day. After each measurement and analysis operation, the controller stores the long-term average of the results within the device memory. When the controller, in conjunction with the real-time clock signal, determines that a measurement and analysis session is due, it begins a measurement procedure illustrated in FIG. 3.

FIG. 3 is a flow chart illustrating a procedure for measuring the stimulated potential, reducing the polarization artifact, setting sensing sensitivity (gain), and determining the minimum stimulation amplitude for safely activating the heart in the illustrative embodiment of the invention. Although the stimulus duration remains constant throughout the procedure in this embodiment of the device, it is to be understood that varying either or both the stimulus duration and amplitude to adequately stimulate the heart is considered to be within the scope of this invention. Although the external programmer may set the configuration of the device to stimulate and sense signals on the lead 16 in either the unipolar or bipolar modes, the selected mode should remain constant throughout the procedure of FIG. 3.

When detecting heart transplant rejection, the best results are attained when the polarization artifact is optimally reduced to a level that is small in comparison to sensed stimulated potentials and intrinsic cardiac events. Using some leads, a directly recorded tip intracardiac electrogram does not produce suitable signals for heart rejection analysis no matter how the stimulation parameter settings are programmed, unless the device minimizes the polarization artifact. This method may be called charge balancing because its goal is to determine a combination of charges delivered in the two positive phases and the single negative phase of the stimulus waveform which results in an acceptably small polarization artifact.

The polarization artifact reduction procedure of FIG. 3 includes nine sub-procedures: start signature 50, initial artifact reduction 51, automatic gain 52, initial stimulated activity threshold 53, vario 54, final artifact reduction 55, final stimulated activity threshold 56, stimulated potential sampling 57, and end signature 58. The procedure ends with wait state 59. In the first seven sub-procedures (50 to 56), the device performs polarization artifact reduction and automatically adjusts the sensing amplifier gain and the stimulus pulse amplitude. We refer to these first seven sub-procedures as the polarization artifact reduction procedure. In the stimulated potential sampling 57 sub-procedure, the device performs the cardiac rejection determining operation.

The controller 11 performs the polarization artifact reduction procedure, beginning with the start signature 50 sub-procedure, when any of the following events occur: a system hardware or software reset, an authorized external device sends a "start procedure" command using telemetric communication, an internal timer set to periodically restart the procedure times out, or the delivered stimulus fails to stimulate a response by the heart in three consecutive stimulus cycles.

In addition to reducing the polarization artifact, the procedure of FIG. 3 addresses fusion events, another problem creating difficulties when attempting to detect cardiac transplant rejection. Fusion events are natural cardiac depolarizations occurring simultaneously with at least some portion of the stimulated potential polarization which changes the morphology of the sensed intracardiac electrogram signal. The preferred embodiment of the invention addresses fusion problems by elevating the cardiac stimulation rate to a level higher than the natural rate. When the event initiating the polarization artifact reduction procedure occurs, the controller performs initialization operations. In the usual operation of the cardiac stimulation device, when the device is not performing the polarization artifact procedure, software continuously updates an average of cardiac cycle interval lengths (stimulated or sensed). The preferred embodiment of the invention determines a weighted running average of interval lengths by adding the current interval to three times the running average and dividing this result by four. Determining the average in this manner is economical in terms of memory and current usage. Upon the event initiating the procedure, software converts the aforesaid running average interval into a rate and begins overdriving the average rate by a predetermined overdrive increment (for example, 25 bpm), but limiting the rate to a programmed maximum. The device continues to pace at this overdrive rate for the entire polarization artifact reduction procedure which endures, for example, for two to three minutes. To prevent the device from constantly boosting the rate in a positive feedback loop, it discontinues the updating of the running average of cardiac interval durations whenever it is overdriving the natural rate.

The purpose of the start signature 50 subprocedure is to provide notification to anyone monitoring the cardiac signal that the device is beginning an operation which will automatically alter important stimulus parameters. Normally, a cardiac stimulation device generates a stimulus once each cardiac cycle (unless the heart beats naturally in a timely manner) upon the time-out of an internal timer. In the start signature 50 sub-procedure, the device provides the notification operation by generating a second pulse shortly after the stimulus. The time interval between pulses (for example, 75 msec) is sufficiently short so that the second pulse is within the refractory period, when it cannot stimulate the heart muscle. The paired pulses are called signature pulses. If the event initiating the polarization artifact reduction procedure is the periodic time-out of the internal timer, then the amplitude of the signature pulses is the value determined in the last threshold search operation, the stimulation threshold plus a safety margin predetermined to insure that the stimulus will normally generate a response. If any other event starts the procedure, the signature pulse amplitude is 7.5 V.

In the preferred embodiment of the invention, if the amplitude of the signature pulse delivered in block 50 of FIG. 3 is 7.5 V, then the controller 11 sets the stimulus pulse amplitude to 3.75 V for the initial artifact reduction 51 sub-procedure to be described. This reduction in amplitude is necessary due to the difficulty in reducing the stimulation polarization artifact at high pulse amplitudes. If the signature pulse amplitude is the stimulation threshold plus a safety margin, the controller continues to generate this amplitude for subsequent pulses.

After delivering the signature pulses, the controller performs the initial artifact reduction 51 sub-procedure. The procedure also enters initial artifact reduction 51 if the stimulation amplitude is determined by the vario 54 operation, hereinafter described, and this stimulation fails to evoke a cardiac response for three consecutive stimulation cycles while the device is operating in one of the sub-procedures following initial artifact reduction but prior to end signature 58. The procedure also recycles to the beginning of the initial artifact reduction 51 sub-procedure upon a single non-consecutive residual artifact test failure (this test is discussed below) during either artifact reduction sub-procedure (51 or 55).

The purpose of residual artifact reduction is to distinguish polarization artifact from stimulated cardiac depolarizations and to eliminate or reduce the amplitude of the artifact. The device does this by generating a stimulating pulse during the absolute refractory period of the heart.

When the cardiac cycle timer expires, the device delivers a stimulus to cause a heart beat then samples the intracardiac electrogram of the stimulated response and calculates activity to determine whether the stimulus successfully stimulated the heart. "Activity" is the measurement of the heart response. In the preferred embodiment of the invention, software determines activity by sampling the output signal of the analog-to-digital block 12 (of FIG. 1) at four millisecond intervals following the blanking period after the stimulus generation, and continues to sample for a sufficient period of time for the heart's response to be detected. The controller 11 synchronizes the timing of the samples to the trailing edge of the negative phase of the stimulation pulse, with the first sample taken at the first multiple of four milliseconds which occurs after the blanking period. To determine activity, software acquires and digitally double integrates six samples. In the preferred embodiment of the invention, the samples are in the form of delta modulator values or readings, in accordance with U.S. Pat. No. 4,692,719, mentioned earlier herein. These delta modulator values are measurements of the sensed signal amplitude difference between a current sample and a previous sample. The double integration procedure requires the accumulation of two sums, the first integral sum and the second integral sum which software initializes to zero before the first sample following the stimulus pulse. Software produces the first integral sum by adding the value of the current sample to the sum of the previous samples. Software derives the second integral sum by adding the value of the current first integral sum to the sum of the previous first integral values. The final double integral summation value represents the activity of the heart's response to the stimulation pulse. When the activity value exceeds a predetermined value, it indicates the occurrence of a responsive heartbeat. The result of the first integration reconstructs the time waveform of the intracardiac signals and the result of the second integration expresses the area under the waveform curve.

Figure 5:
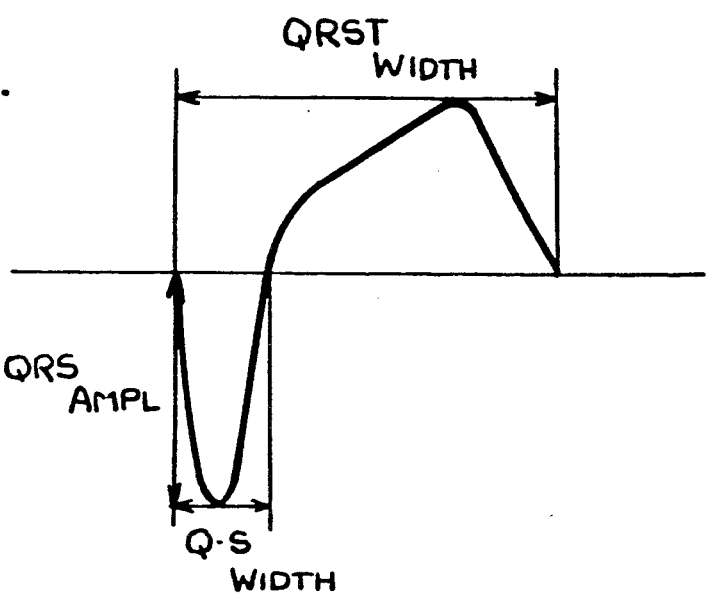
FIG. 5 is a sample illustration of a stimulated intracardiac electrogram QRST-complex waveform using sensing in the unipolar configuration.
Figure 6:
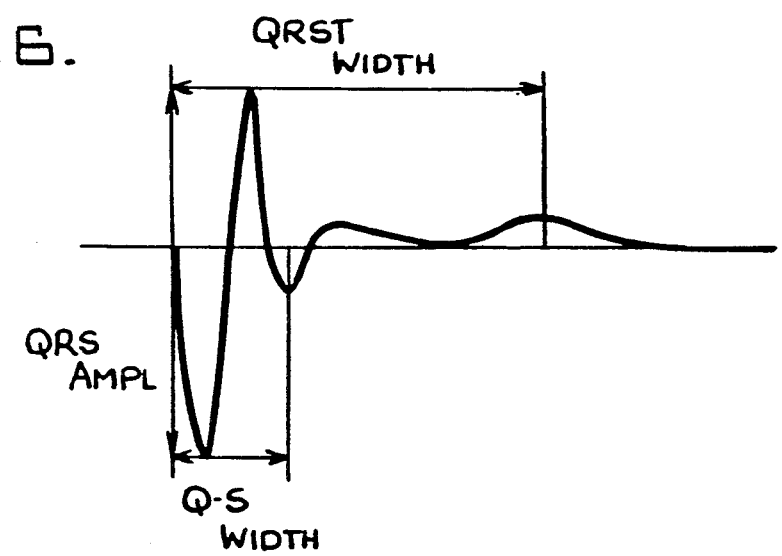
FIG. 6 is a sample illustration of a stimulated intracardiac electrogram QRST-complex waveform using sensing in the bipolar configuration.

Signals sampled using bipolar sensing may display a biphasic morphology within the six samples. Unipolar signals are typically monophasic and negative. The Q-S width portion of FIG. 5 and FIG. 6 illustrate this difference. Double integration samples acquired when the sensing circuits are configured in the bipolar mode would be too inaccurate for clinical usage. Accordingly software accumulates the absolute value of the intermediate sum into the final sum while performing in the bipolar sensing mode. Since signals measured when circuits are configured in the unipolar configuration nearly always have a negative polarity, software reverses the sign of the intermediate integral sums before accumulating the second integral sum. If such a result is negative in sign, software sets it to zero.

Software compares the activity to a stimulated activity threshold value derived in the most recent stimulated activity threshold operation (53 or 56 of FIG. 3). (If no stimulated activity threshold operation has taken place under the current stimulation conditions, the controller may initialize the stimulated activity threshold value to a low magnitude, even zero, to guarantee that the procedure will not fail unnecessarily when the value is not known.) If activity is greater than the stimulated activity threshold value, software determines that the pulse successfully stimulated the heart. If the pulse does not stimulate the heart, any further data analysis for the current cardiac cycle ends. It is possible that the low activity value may actually indicate a fusion event rather than a failure to stimulate the heart. Since the device can avoid the problems arising from fusion events by further overdriving the pacing rate, it responds to the detected failure to stimulate the heart by increasing the pacing rate by 15 bpm for a single failure and by 10 bpm more to a total of 25 bpm for the second of two consecutive failures. Software limits the overdrive rates to the programmed maximum. To prevent the device from failing to sense a subsequent natural heartbeat after a single failure, the device begins sensing after a short delay following the determination that the heart did not respond to the stimulus. In the case of either two or three consecutive failures, the device issues a backup stimulation pulse soon after the last of such inadequate stimulus pulses (about 125 msec). The backup stimulus has twice the pulse duration of the original stimulus to sustain the patient in case the patient's health is dependent on such stimulation. If the stimulus fails to activate the heart on three consecutive cycles, the operation of the procedure either restarts the initial artifact reduction 51 sub-procedure if this is the first failure within an artifact reduction procedure, or terminates the procedure by delivering the end signature pulses in block 58 if this is the second such failure. The device responds to the failure to stimulate the heart in this manner for all sub-procedures of the artifact reduction procedure, except that the method for the vario 54 sub-procedure differs slightly, as will be described below.

Upon successful stimulation of the heart, the device delivers an additional pulse, called a refractory pulse, during the heart's refractory period (for example, about 125 ms after the stimulus pulse). By generating this pulse during the absolute refractory period, after which any signal sensed is due primarily to polarization artifact, the device distinguishes the polarization artifact from either stimulated or natural cardiac depolarizations. Following the refractory pulse, the device performs two sampling operations of the polarization artifact signal. In the first sampling operation, software performs residual artifact sampling after the trailing edge of the refractory pulse using the same sampling procedure (six samples acquired at four millisecond intervals) as was performed while determining the activity following the stimulus pulse. In the second sampling operation, the device measures the polarization artifact to derive an artifact reduction parameter. Software performs an artifact reduction parameter accumulation on the first two or three samples acquired during the first sampling operation, in a manner similar to that done in connection with the double integration to derive the activity, except that the artifact reduction parameter accumulation persists for two or three samples rather than six and the second summation accumulates the intermediate sum without changing the sign of the first integral of the signal. Experimentally, these two or three samples were shown to characterize the peak amplitude of the first phase of a typically biphasic polarization artifact for the purpose of performing adjustments to reduce this artifact as will appear in greater detail below.

Figure 4:
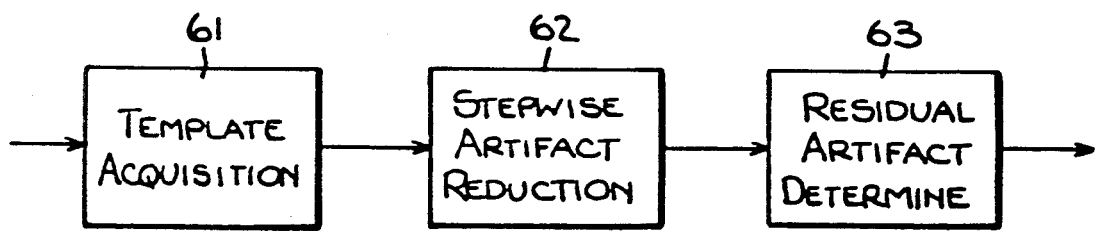
FIG. 4 is a flow chart illustrating the operational steps of the stimulation polarization artifact reduction function performed by the illustrative embodiment of the invention.

In both artifact reduction sub-procedures (51 and 55), the controller 11 performs the operations, shown in FIG. 4, of template acquisition 61, stepwise artifact reduction 62, and residual artifact determination 63. During template acquisition 61, the controller measures the underlying intracardiac electrogram signal detected during refractory sampling in the absence of a refractory pulse. The purpose of stepwise artifact reduction 62 is to automatically adjust the precharge duration of the triphasic stimulus waveform in vivo, in a small step within each cardiac cycle, to eliminate or reduce the polarization artifact. The device varies the precharge duration until the polarization artifact is small in comparison to the ventricular stimulated response. In the residual artifact determination 63, software corrects the intracardiac electrogram signals measured following a refractory pulse to remove therefrom the underlying intracardiac electrogram signals which were sampled during template acquisition 61. Software then uses the resulting residual artifact parameter for device self-diagnosis and control as will appear in greater detail below.

In the first task of the template acquisition 61 operation, the controller initializes the precharge duration to the value determined in the most recent successful initial or final artifact reduction sub-procedure. Software run by the controller performs this task only if the stimulus pulse amplitude is 3.75 V. If the stimulus pulse amplitude is the previously determined stimulation threshold plus margin value, the device is performing the polarization artifact reduction procedure for the purpose of maintenance rather than because of a form of system failure and there is no reason to change the precharge duration in a properly functioning system. Following this initialization task, the stimulus pulse amplitude and precharge duration remain unchanged throughout the template acquisition 61 and the stepwise artifact reduction 62 operations. To allow the controller to measure the underlying electrogram signal occurring during the sampled portion of the heart's refractory period, it sets the refractory pulse amplitude to zero volts for template acquisition 61. The precharge duration for the refractory pulse is the same as that for the stimulus pulse. Template acquisition 61 lasts for eight cardiac cycles, during which software measures and accumulates samples of the underlying intracardiac electrogram signal during both the aforesaid six sample sampling operation to create a residual artifact template for correcting the residual artifact signal, and the two or three sample sampling operation to create an artifact reduction template which is necessary for performing stepwise artifact reduction. The templates are created by summing and averaging the double integral values obtained during the eight cardiac cycles.

During stepwise artifact reduction 62, while generating both the stimulus and the refractory pulses using the triphasic waveform of FIG. 2 (precharge, stimulus, and postcharge), the device 1 varies the precharge duration until the refractory polarization artifact is small in comparison to the ventricular stimulated response. The controller sets the pulse amplitude for the refractory pulse to 2.5 V if the stimulus pulse amplitude is 3.75 V, otherwise the device maintains a refractory pulse amplitude of stimulus threshold plus margin (the same amplitude as for the stimulus pulse). A stimulus pulse amplitude of 3.75 V implies that the threshold stimulus pulse amplitude is not known. Since the threshold stimulus pulse amplitude may range from 3.75 V down to 0.5 V or lower and the precharge duration which minimizes the polarization artifact varies nearly proportionally to the stimulus pulse amplitude, minimizing the polarization artifact starting from a refractory pulse amplitude of 2.5 V will provide a mid-range precharge duration to best reduce the artifact throughout the range of amplitudes which will be spanned in the subsequent vario 54 operation.

The device 1 samples and accumulates the artifact reduction parameter for each cardiac cycle and subtracts the artifact reduction template from the artifact reduction parameter, then adjusts the precharge duration by about 30 usec in the direction of the sign of the subtraction result. Because the polarization artifact represents a sensing amplifier's (not shown) response to an offset voltage (polarization) on the lead electrodes, the controller 11 uses the polarity of the first phase of the artifact to determine which direction to change the precharge duration for the refractory pulse to further reduce the artifact amplitude. The precharge duration of the stimulus pulse remains unchanged at this time. The controller increases the precharge duration if the first phase of the polarization artifact is positive, otherwise it decreases the duration. The output generator 13 and sensing and polarization controller 15 are designed to function properly in combination with wide variety of leads 16. Leads are constructed from many types of materials and have very different characteristics (for example, impedances). An excessively large or small precharge duration value may create a large artifact which the artifact reduction operation 62 cannot reduce. For this reason, software imposes predetermined upper and lower limits on precharge duration. The value of these limits is based on electrical characteristics of the circuits and leads. If the controller attempts to increase the precharge duration above the upper limit or decrease the precharge duration below a lower limit (this is usually zero usec), then the stepwise artifact reduction operation 62 is complete. While the device is performing the stepwise artifact reduction step within the prescribed limits, at some point further changes in precharge duration will either completely eliminate the polarization artifact or cause it to reverse polarity, depending on the sensing amplifier gain, stimulus energy, and characteristics of the electrode system. A polarization reversal occurs when the change in precharge duration causes the result of the subtraction to change in sign as compared to the result of the previous cycle. After a predetermined number of polarization reversals (for example, four), the controller determines that the polarization artifact is sufficiently reduced and the sub-procedure sequences to the residual artifact determination 63. The device requires a number of polarization reversals to provide protection against incorrectly determining the proper precharge duration in the presence of fusion events. Because some leads produce only a very minor polarization artifact for the procedure to eliminate, the controller also terminates the stepwise artifact reduction operation 62 if the sub-procedure endures longer than a predetermined number of steps (for example, 128). The precharge duration resulting from the residual artifact determination operation is the optimum precharge duration.

In the residual artifact determination 63 operation which occurs for eight cardiac cycles following the stepwise artifact reduction 62 operation, the controller 11 first sets the precharge duration of both the stimulus and the refractory pulses to the newly determined optimum precharge duration. The controller maintains the same stimulus and refractory pulse amplitudes in the transition from the stepwise artifact reduction to residual artifact determination. For the eight cardiac cycles of the residual artifact determination 63, software measures and accumulates only the residual artifact value (not the artifact reduction parameter). On the eighth cardiac cycle, the controller divides the accumulated residual artifact by eight and subtracts from it the residual artifact template determined by the previous template acquisition operation 61. This result is the template-corrected residual artifact. In the final operation of the residual artifact 63 operation, the controller saves the optimum precharge duration in memory for usage in future residual artifact reduction operations in case the procedure restarts for a reason other than timed recycling.

Physiological or external noise (for example, 60 cycle noise) is one phenomenon which may influence the operation of the artifact reduction procedure. The device detects such noise by measuring intracardiac electrograms during the heart's relative refractory period. For each sensed signal with an amplitude change greater than a predetermined sensing threshold during the relative refractory period of a cardiac cycle, the controller restarts the refractory period timer and increments the sensing threshold for the remainder of that cardiac cycle. The new sensing threshold endures until a sensed signal greater than such new sensed threshold occurs and restarts the timer and again increments the sensing threshold. After the refractory timer has timed out and prior to the timing out of the cardiac cycle timer, sensed signals inhibit the device from generating stimulus pulses. Once the refractory timer extends beyond the cardiac cycle timer, a sensed signal can no longer inhibit the device from delivering a stimulus pulse. A noise cycle is defined as a cardiac cycle in which the refractory timer extends beyond the cardiac cycle timer due to refractory period recycling. When the device detects a noise cycle, software always suspends the sampling function of the polarization artifact reduction procedure for that cardiac cycle. Because overdriving to elevate the heart rate occurs during this procedure and noise cycle sensing may cause the device to remain in an overdriven state potentially forever, the controller accumulates a noise cycle counter. If noise cycle counter accumulates a count of 256 during a single artifact reduction procedure encompassing blocks 51 and 55 of FIG. 3, the controller jumps to the end signature 58 operation and terminates the procedure, restoring the stimulus pulse amplitude and precharge duration to the results of the most recent successful polarization artifact reduction procedure.

Again referring to FIG. 3, after the successful completion of the initial artifact reduction 51, the controller performs the automatic gain 52 subprocedure only if an external programmer activates an automatic gain function. When enabled, the automatic gain function procedure sets the gain of the sensing amplifier of the sensing and polarization controller 15 by analyzing samples acquired during the absolute refractory period. The automatic gain 52 sub-procedure sets gain so that sensed signals will have a high amplitude, but not so high as to produce saturated signals. Setting the gain in this manner improves the device's natural heartbeat signal sensing operation as well as its signal analysis capabilities while performing the other sub-procedures of FIG. 3. If the automatic gain function is disabled and an automatic stimulus pulse amplitude function is enabled, control of the procedure proceeds to the initial stimulated activity threshold 53 sub-procedure. When enabled, the automatic stimulus pulse amplitude function allows the device 1 to determine a stimulated activity threshold value which, when sensed and measured, indicates the successful stimulation of the heart and the stimulus threshold pulse margin amplitude value necessary to successfully stimulate the heart, as will be described in detail hereinafter. If neither the automatic gain nor the automatic stimulus pulse amplitude function is enabled, control of the procedure jumps to the end signature 58 sub-procedure.

During automatic gain 52 sub-procedure, the device 1 samples the activity of the intracardiac electrogram and responds to the failure to activate the heart in the manner described previously. If the device successfully activates the heart, it continues to sample the intracardiac electrogram for additional samples. The stimulus pulse amplitude for the automatic gain 52 sub-procedure is the same as the amplitude of the stimulus pulse in the initial artifact reduction 51 operation. The term "stimulated potential signal" is intended to refer to signals generated by the heart during the heart's activation wave in response to a stimulated pulse applied to the heart. It primarily refers to the heart's responsive QRS-complex. The total number of samples is intended to encompass the entire stimulated potential signal, including the QRS-complex. The number of samples taken depends on the bandwidth of the sense amplifier in the sensing and polarization controller (block 15 of FIG. 1). The device 1 measures each of the stimulated potential signal samples to find the largest positive value in four consecutive paced cardiac cycles. On every fourth cardiac cycle, if the largest positive sample is less than or equal to a predetermined automatic gain test level of amplitude, then the device increases the gain setting in the sensing and polarization controller by one count. Otherwise, the controller 11 decreases the gain setting by one count. To prevent a potentially unsafe sensitivity setting, the controller 11 limits the gain setting to predetermined maximum and minimum values. If updating the gain would violate either limit, the gain setting remains the same. In either case, the software tests the current amplitude test result against the amplitude test result from the previous four cycle sample. If the largest positive value from the current sample is greater than the automatic gain test level of amplitude and the largest positive value from the previous sample is not, the condition is an automatic gain amplitude test crossing. Upon the occurrence of a predetermined number of automatic gain amplitude test crossings, the automatic gain 52 sub-procedure finishes and, if the external programmer has activated the automatic stimulus pulse amplitude function, control of the procedure moves to the initial stimulated activity threshold 53 sub-procedure. If the automatic stimulus pulse amplitude function is disabled, control of the procedure jumps to the end signature 58 subprocedure.

The purpose of the stimulated activity threshold operation is to measure the "stimulated activity threshold value", which is defined as the activity which distinguishes a stimulation pulse amplitude normally capable of generating a response by the heart from the activity of a stimulation pulse amplitude which does not. The stimulus pulse amplitude for the initial stimulated activity threshold 53 sub-procedure is the same as the amplitude of the stimulus pulse in the previous operation (either the initial artifact reduction 51 or automatic gain 52 sub-procedure), except that software limits the amplitude to a value of the maximum allowable stimulus threshold plus the margin (for example, 3.2 V). During the stimulated activity threshold sub-procedure, the controller measures the activity by sampling and double integrating in the manner described previously, then averages the activity for eight successfully sampled cardiac cycles. During a stimulated activity threshold sub-procedure, the device samples the activity of the intracardiac electrogram and responds to the failure to activate the heart in the manner described previously, with one exception. A failure to stimulate the heart in three consecutive cardiac cycles indicates that the stimulus threshold amplitude is greater than the aforesaid maximum allowable stimulus threshold plus margin. If the stimulus pulse amplitude is less than such threshold plus margin, then the controller 11 restarts the procedure by initializing the stimulus pulse amplitude to 3.75 V and looping back to the initial artifact reduction 51 operation. Otherwise, software terminates the procedure by setting the stimulus pulse amplitude to a safe level (for example, 7.5 V) and jumping to the end signature 58 sub-procedure.

After measuring the averaged activity for the eight cycles referred to above, software performs a residual artifact test by comparing the magnitude of the corrected stimulated activity (the averaged activity minus the residual artifact obtained during the artifact reduction sub-procedure 51 or 55) to a preset multiple (for example, eight) of the magnitude of the residual artifact. If the magnitude of the corrected stimulated activity is too small, the system fails the residual artifact test since it is unable to sufficiently reduce the artifact. A residual artifact test failure may indicate a device malfunction or a physiological anomaly such as fusion events. To determine the reason for the test failure, the controller restarts the procedure by initializing the stimulus pulse amplitude to 3.75 V and looping back to the initial artifact reduction 51 operation. If the system fails the residual artifact test for more than a predetermined number of consecutive attempts (for example, two), the controller terminates the procedure by setting the stimulus pulse amplitude to a safe level (for example, 7.5 V) and jumping to the end signature 58 sub-procedure. If the procedure terminates in this manner in a predetermined number (for example, four) of consecutive attempts, the controller 11 prevents further attempts by disabling the procedure. Only intervention by an external programmer over the telemetry link will re-activate the procedure. If the averaged activity signal passes the residual artifact test, software derives the stimulated activity threshold value by subtracting the residual artifact found in the last residual artifact determination operation (block 63 of FIG. 4) from the averaged activity and multiplying the result by a predetermined fractional factor. This factor defines the minimum activity signal that will indicate a successful stimulation of the heart, taking into consideration the average signal level and the detected noise level (the residual artifact), and setting the threshold level between them. In the preferred embodiment of the invention, the value of the factor is either 50 percent or 25 percent, respectively, for signals sensed in the bipolar and unipolar configurations.

After the successful completion of initial stimulated activity threshold block 53 (FIG. 3), the controller 11 performs the vario 54 sub-procedure to determine the stimulation pulse amplitude normally capable of giving rise to a response by the heart. The beginning stimulus pulse amplitude for the vario operation is the same as the amplitude used when performing the initial stimulated activity threshold 53 sub-procedure. For each vario cardiac cycle, the controller 11 measures the activity as described previously. If the stimulus pulse succeeds in stimulating a cardiac response, the controller decreases the stimulation amplitude by a preset step size (for example, 0.1 V) for the next cardiac cycle. If the stimulus fails to evoke a response, the stimulation amplitude remains the same. After three consecutive failures, the vario operation is complete and the controller increases the stimulation amplitude by a preset voltage margin (0.6 V in the preferred embodiment of the invention) and the device begins performing the final artifact reduction 55 sub-procedure. The vario operation will also terminate without failing to generate a cardiac response if the software decrements the stimulation amplitude below a predetermined minimum stimulation level, such as 0.5 V.

If the device 1 detects a noise cycle during the vario operation, software restarts the stepwise vario function by initializing the stimulus pulse amplitude to the original level for the current subprocedure. This is done to avoid generating pulses which are inadequate to stimulate the heart during continuing noise cycles. To limit the time a patient is subject to the possibly inadequate stimulus pulse amplitudes tested within the stepwise vario operation, software limits the number of cardiac cycles in which natural activity inhibits pacing or noise occurs during the sub-procedure. If the number of such cardiac cycles surpasses this limit (for example, 32 cycles), the controller 11 terminates the procedure by jumping to the end signature 58 sub-procedure after setting the stimulus pulse amplitude to the value determined in the last vario procedure or, if the device is performing the procedure because of a failure to stimulate the heart, to a safe level (for example, 7.5 V).

After performing the vario 54 operation, software controls the final artifact reduction 55 subprocedure to minimize the magnitude of the polarization artifact after the pulse amplitude is set to the newly determined stimulation threshold plus margin value. Operations of the final (block 55) and initial (block 51) artifact reduction sub-procedures are identical except for possible differences in the generated stimulation pulse amplitudes.

In the final stimulated activity threshold 56 sub-procedure, the device determines the stimulated activity threshold value for cardiac signals stimulated from pulses having the newly determined stimulation amplitude. Other than possible changes in stimulation pulse amplitude, the final (56) and initial (53) stimulated activity threshold sub-procedures are the same.

The device 1 performs the stimulated potential sampling 57 sub-procedure only if the preceding sub-procedures and test succeeded. If the automatic stimulus pulse amplitude function is enables, the stimulation amplitude is the stimulation threshold plus margin value determined in the vario 54 sub-procedure. If the automatic stimulus pulse amplitude function is enables, the device continues to monitor the activity of the stimulated potential in the manner previously described to determine whether the stimulus pulse amplitude (stimulus threshold plus margin) remains sufficient to activate the heart. Normally, cardiac rejection monitoring requires a physician to enable the automatic stimulus pulse amplitude function to allow the device to ignore stimulated potential measurements for cardiac cycles in which the stimulus fails to stimulate the heart or when fusion events occur.

In the stimulated potential sampling 57 subprocedure to be described in greater detail hereinafter in connection with the description of FIG. 8, the device 1 performs a cardiac rejection determining operation while continuing to stimulate at the fixed overdrive rate. This operation may occur on every stimulated cardiac cycle or only on selected cycles as controlled by the external programmer. After a single failure to generate a cardiac response, the controller 11 increases the stimulation rate by a predetermined amount (for example, 15 bpm) in case the device incorrectly classifies a fusion event as the failure to stimulate the heart. After two consecutive failures, the controller increases the stimulation rate by a further predetermined amount (for example, to a total increase of 25 bpm) and delivers a backup stimulation pulse in the manner described previously. After three consecutive failures, the controller delivers a backup stimulation pulse, increases the stimulation pulse amplitude to a safe level, and restarts the polarization artifact reduction procedure.

Figure 7:
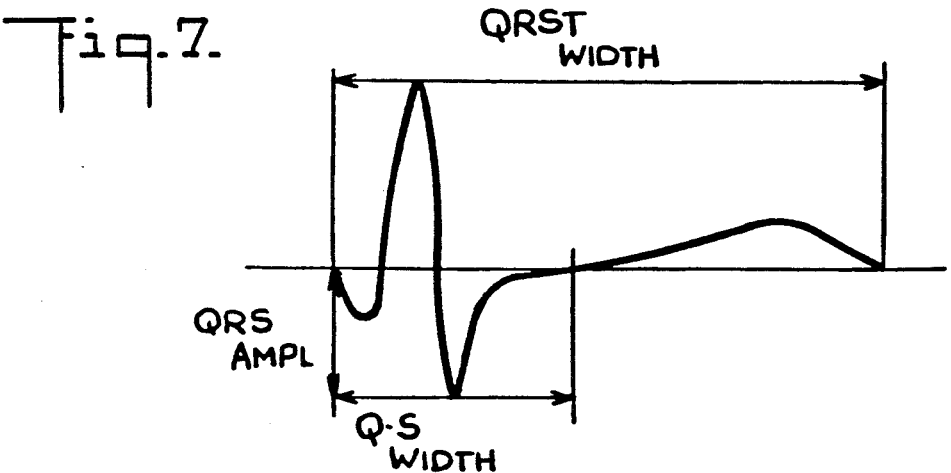
FIG. 7 is a sample illustration of an intrinsic intracardiac electrogram QRST-complex waveform using sensing in the unipolar configuration.
Figure 4:
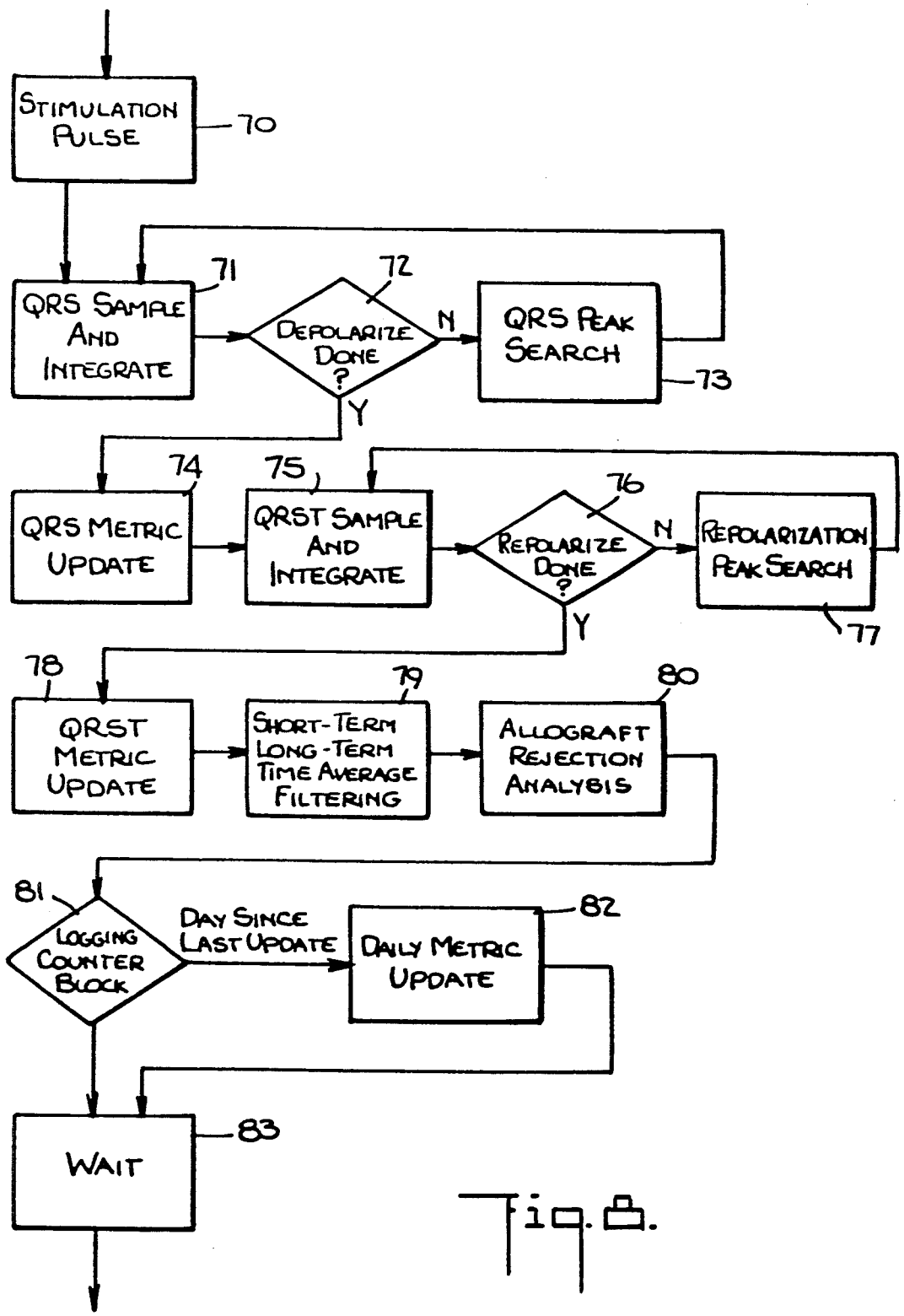

FIG. 5 illustrates a typical stimulated intracardiac electrogram waveform as detected by the device 1 when it is sensing in the unipolar mode. Pertinent measurements are labelled therein. For each measured cardiac cycle, the controller 11 governs the sampling and measurement of each of the following stimulated potential waveform metrics: the QRS amplitude and Q-S width; the baseline adjusted peak positive and negative polarization magnitudes and the total peak-to-peak amplitude; and the QRST area and integrated magnitude. Software measures, averages and stores a time history record of these parameters for the purpose of detecting diagnostic changes over time. Commands from an external programmer using telemetry enable or disable the selection of a particular metric for analytical purposes. FIG. 6 illustrates a typical stimulated intracardiac electrogram waveform as detected by device 1 when it is sensing in the bipolar mode. The unipolar signal of FIG. 5 has a more simple monophasic waveform than the bipolar signal, leading to more reliable rejection decision-making with unipolar sensing. FIG. 7 illustrates a typical intrinsic intracardiac electrogram waveform as detected by device 1 when it is sensing in the unipolar mode. This signal is more complex than the stimulated polarization waveform detected using bipolar sensing (FIG. 6). This reduces the diagnostic reliability further. In addition, the intrinsic waveform of FIG. 7 is more subject to cycle-to-cycle and implant-to-implant variability than either of the stimulated waveform signals of FIG. 5 or FIG. 6.

Figure 9:
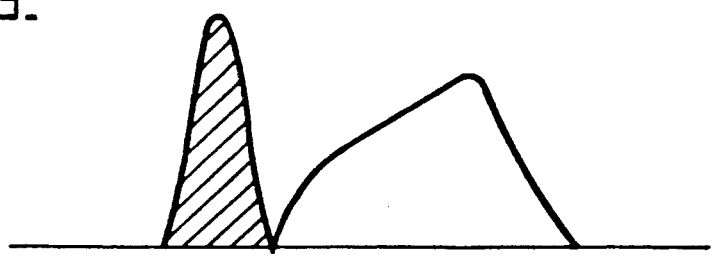
FIG. 9 is an illustration of the morphology of a stimulated intracardiac electrogram QRS-complex waveform using sensing in the unipolar configuration as is processed by the invention.
Figure 11:
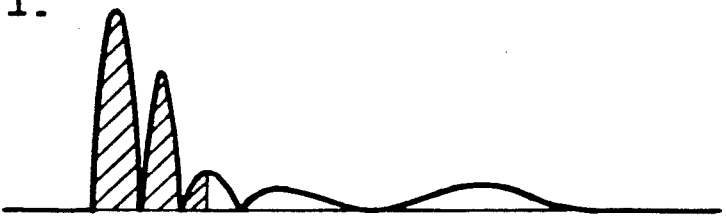
FIG. 11 is an illustration of the morphology of a stimulated intracardiac electrogram QRS-complex waveform using sensing in the bipolar configuration as is processed by the invention.

FIG. 8 is a flow diagram of the operations performed by software to measure and analyze the stimulated potential waveform metrics within a single cardiac cycle. For the purposes of heart transplant rejection analysis, stimulated potential depolarization defines the QRS-complex and combined stimulated potential depolarization and repolarization defines the QRST-complex. If the device successfully activates the heart, it continues to sample the intracardiac electrogram for additional samples. The total number of samples is set to span the entire QRST-complex. After the device generates a stimulation pulse in block 70 of FIG. 8, it samples the response signal in the form of delta modulator values, in accordance with U.S. Pat. No. 4,692,719, mentioned earlier herein. The sampling takes place at four millisecond intervals in the same manner as the activity was determined. The device 1 then derives and stores the value of the single and the double integral for the samples in QRS sampling block 71. The single integral of the sample has a signed value indicating the polarity of the waveform. For signals sensed in the unipolar mode, a negative single integral shortly after the stimulus is the stimulated depolarization. Later the single integral becomes positive, indicating repolarization of the cardiac tissue as shown in FIG. 5. Because signals sensed in the bipolar mode are not monophasic, it is impossible to accurately distinguish cardiac depolarization from repolarization. The double integral of the intracardiac electrogram is the area of the polarization waveform. In QRS sampling block 71, the double integral is the depolarization area as is illustrated by the shaded area in FIG. 9 when the device is sampling in unipolar mode and as is illustrated by the shaded area in FIG. 11 for bipolar sensing. Recall that in the double integral determination for activity, software integrates the absolute value of the first integral for signals sensed in the bipolar mode and changes the sign of the first integral before performing the second integration for unipolar signals. In the preferred embodiment of the invention, software does not continue to follow this convention while measuring the QRS and QRST stimulated potential signals. Instead, for both the unipolar and bipolar sensing modes, the device reverses the sign of the first integral and then integrates the reversesigned value of the first integral to determine the second integral sum.

In logic block 72, software searches for the point of change from depolarization to repolarization. When the device is sensing in unipolar mode, the change from depolarization to repolarization is that one of the samples at which the single integral switches from a negative to positive value. In FIG. 5, this point occurs at the end of the portion of the waveform denoted as the Q-S width for the unipolar mode. Because a noisy intracardiac electrogram signal may have a number of these zero-crossing occurrences, the device requires some means to define a valid polarization change. The preferred embodiment of the invention defines a first window, specified as the "QRS window", within which the polarization may change from negative to positive and a second window, named the "QRST window", wherein the polarization begins as a positive quantity but may change to negative or zero value. The zero-crossing point within the first window defines the end of the QRS-complex. A preset sample number in the second window defines the end of the QRST-complex and the limit for the QRST window. Signals sensed in the bipolar mode are not monophasic but, instead, are multiphasic as shown in FIG. 6, therefore no means exists to determine the end of the QRS-complex by analyzing the double integral value. In the bipolar case, software does not search for the crossing from negative to positive polarity but, instead, uses a predetermined sample number as the end of the QRS-complex and uses this number to define the QRS window.

When the device is sensing in unipolar mode, software performs the two tests to find the end of the QRS-complex in logic block 72. If the value of the first integral of the electrogram is negative prior to its updating for the current sample and becomes positive after updating and the sample number is within the range previously defined as the QRS window, then software progresses to the QRS updating step in block 74. The procedure also terminates QRS sampling and proceeds to block 74 if the sample number is the last in the window. Otherwise, software performs the QRS peak search in block 73 before acquiring the next QRS sample in block 71. When the device functions in bipolar mode, software does not test the polarity of the integral to determine when to advance from one state to the next. Rather, software advances the state only upon reaching the predetermined QRS window limit.

In block 73, software performs the QRS peak search. The peak is defined as the maximum negative amplitude of the electrogram when sensing in unipolar mode. The peak is defined as the peak-to-peak amplitude of the electrogram when sensing in bipolar mode. For the first sample following the stimulus pulse, software reads the sample and stores its value into each of the negative QRS peak memory location and the positive QRS peak memory location. This initializes each peak memory location for the current cardiac cycle. For subsequent samples, software writes the first integral to the negative QRS peak memory location only if the value of the first integral is a larger negative number than the previously stored peak negative value. Likewise, software writes subsequent first integral values to the positive QRS peak memory location only if the value of the first integral is a larger positive number than the previously stored peak positive value.

In block 74, software updates the QRS waveform metrics. In unipolar sensing mode, software loads the stored negative QRS peak value, changes its sign, and stores it into a QRS amplitude memory location. In bipolar sensing mode, software loads the stored positive QRS peak value, subtracts from it the negative QRS peak value, and stores the difference into the QRS amplitude memory location. Software loads the double integral value for the current sample (after it was updated in block 71) and stores it into a QRS area memory location. Note that the QRS area value is always positive under the current convention for signals sensed in both the unipolar and bipolar modes because any negative value is forced to zero. Software stores the current sample number, which is a count of the number of samples following the stimulation pulse, into the Q-S width memory location.

Figure 10:
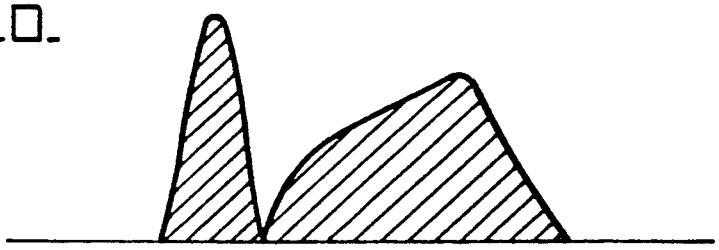
FIG. 10 is an illustration of the morphology of a stimulated intracardiac electrogram QRST-complex waveform using sensing in the unipolar configuration as is processed by the invention.
Figure 12:
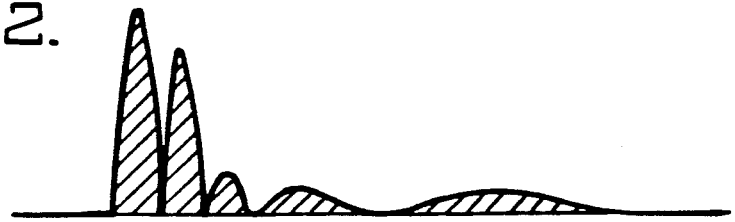
FIG. 12 is an illustration of the morphology of a stimulated intracardiac electrogram QRST-complex waveform using sensing in the bipolar configuration as is processed by the invention.

The device 1 continues to sample, process and analyze the data and store the values of the single and the double integrals for the four msec samples in QRST sampling block 75. The function of QRST sampling block 75 is intended to track the repolarization of the heart. Note that the single and double integral values are not reinitialized between the QRS and QRST-complex sampling operations. In the QRST sampling block 75, the single integral values are positive when the device is sensing in unipolar mode because the stimulated potential waveform tracks the repolarization of the heart. In QRST sampling block 75, the double integral is the depolarization area and the repolarization area as is illustrated by the respective left and right shaded areas in FIG. 10 when the device is sampling in unipolar mode and as is illustrated in FIG. 12 for bipolar sensing, wherein the two left and the center shaded areas correspond roughly to cardiac depolarization and the two right shaded areas approximate the heart's repolarization.

In logic block 76, software integrates the electrogram to analyze the repolarization signal in the same manner as it analyzed the QRS signal. Logic block 76 tests for the end of repolarization sampling by checking the current sample number against the predetermined total number of samples in the QRST window. The procedure also finishes QRST sampling and proceeds to block 78 if the current sample number is the last in the QRST window. Otherwise, software performs the repolarization peak search in block 77 before acquiring the next QRST sample in block 75.

In block 77, software performs the repolarization peak search in the same manner as was done in the QRS peak search in block 73, except that the procedure updates new memory locations, the negative QRST peak and the positive QRST peak.

In block 78, software updates the QRST waveform metrics. Software loads the repolarization peak value, the positive QRST peak when sensing in unipolar mode and the positive QRST peak minus the negative QRST peak when sensing in bipolar mode, and stores this value into a T-wave amplitude memory location. Software loads the double integral value for the current sample (after it was updated in block 75) and stores this value into a QRST area memory location. The influence of depolarization and repolarization will tend to cancel when determining the QRST area. Software derives a measurement of the absolute value of the QRST area (the sum of the absolute values of each double integral) by subtracting the QRST area memory location (containing a negative representation of depolarization and a positive representation of repolarization) from twice the QRS area memory location (containing a positive representation of depolarization). In this manner, one positive representation of both the depolarization and repolarization signals is summed and stored while a positive and negative representation of the depolarization area are cancelled. This is a simple and efficient software operation. Software stores this result in the absolute QRST electrogram memory location.

When sensing in unipolar mode, software derives another metric, the QRS amplitude to duration ratio, by dividing the QRS amplitude by the Q-S width. This parameter appears to have high clinical utility in detecting the early stages of transplant rejection.

For each of the metrics derived and stored in blocks 74 and 78, software performs time averaging in block 79. In general, a change in a diagnostic stimulated potential waveform metric over a period of one or two days is an indication of transplant rejection. Short-term non-diagnostic changes in the waveform metrics, arising from day to day (20% changes are not uncommon) and circadian rhythm variability as well as randomness arising from external influences such as drug therapy and fusion events, impede the detection of transplant rejection. In addition, long-term drift in waveform metrics, mainly caused by changes in lead impedance over time, makes rejection diagnosis uncertain. The system addresses both short-term and long-term variability problems by averaging the data using low-pass filtering techniques. For each acquisition of metric data, the device low-pass filters the data on a short-term basis to provide an averaged characterization of the metric data over roughly the last half day and further low-pass filters the data on a long-term basis to characterize the metric data over about a four day period. Software then compares the short-term with the long-term metric data averages. If the metric data average changes by more than a predetermined threshold value, software stores a code in memory designating the nature and time of the test result.

In the preferred embodiment of the invention, the device activates the polarization artifact reduction procedure and determines each of the previously discussed metrics about every ten minutes. In the averaging block 79, software performs short-term and long-term average filtering using recursive filtering techniques which are well-known in the art of signal processing. The short-term filter memory is described by the following equation:

$$S_i = \frac{15}{16} S_{i-1} + X_i,$$

where $S_i$ is the current short-term filter memory representing sixteen times the short-term metric data average, $S_{i-1}$ is the last previous short-term filter memory, and $X_i$ is one of the updating metric data values. The long-term filter memory is described by the following equation:

$$L_i = \frac{127}{128} L_{i-1} + X_i,$$

where $L_i$ is the long-term filter memory representing 128 times the long-term metric data average, $L_{i-1}$ is the last previous long-term filter memory, and $X_i$ is again one of the updating metric data values.

After processing the data in averaging block 79, software analyzes the processed data in allograft rejection analysis block 80 for the purpose of detecting transplant rejection. For each metric, after updating the short-term and long-term averages, software compares the two average values. There is at least one programmer-set comparison limit value corresponding to each metric value in memory. There are also programmer-set diagnostic importance factors for each metric type. If the result of the comparison exceeds a limit value for a particular metric, software increments a decision-making parameter (called the allograft rejection control parameter) by a factor, the value of which depends on the result of the comparison and the diagnostic importance of the metric. If the allograft rejection control parameter exceeds a preset value after compiling the data from all metrics, software stores the value and the time (from a real-time clock function as is known in the art of implantable devices) in diagnostic notification memory locations.

Figure 13:
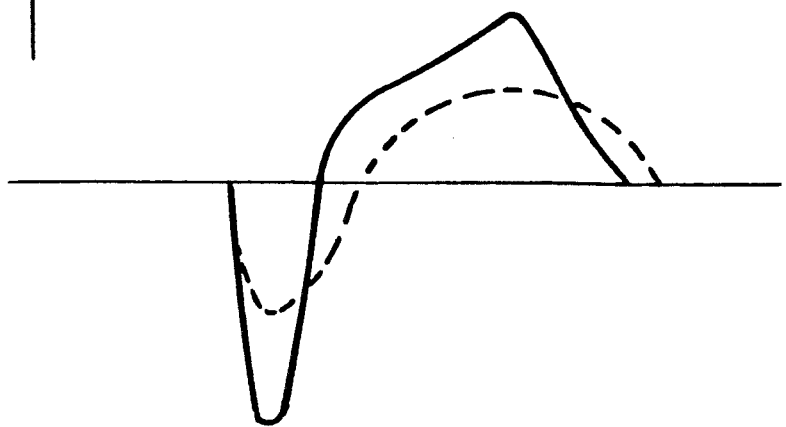
FIG. 13 is a sample illustration showing the changes which occur in a stimulated intracardiac electrogram QRST-complex waveform using sensing in the unipolar configuration in the presence of allograft rejection.
Figure 14:
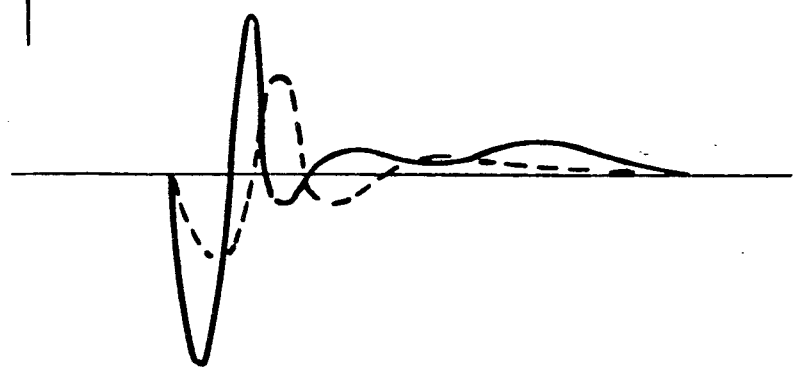
FIG. 14 is a sample illustration showing the changes which occur in a stimulated intracardiac electrogram QRST-complex waveform using sensing in the bipolar configuration in the presence of allograft rejection.
Figure 15:
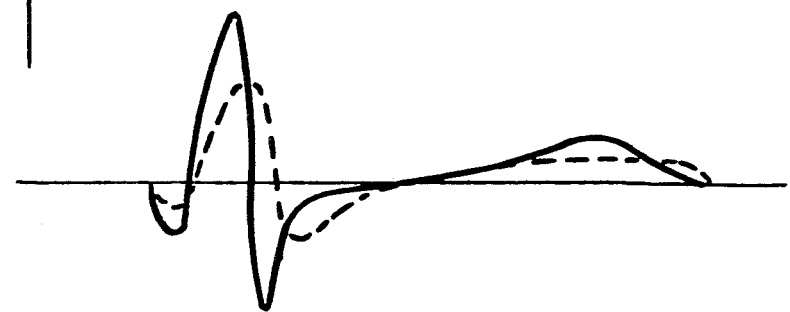
FIG. 15 is a sample illustration showing the changes which occur in an intrinsic intracardiac electrogram QRST-complex waveform using sensing in the unipolar configuration in the presence of allograft rejection.

The purpose of the allograft rejection control parameter is to detect transplant rejection through changes in the intracardiac electrogram waveform. FIG. 13 illustrates the type of changes in the unipolar-sensed electrogram which result from allograft rejection. The solid line in FIG. 13 denotes the normal waveform. The broken line shows the way the waveform is changed when rejection occurs. FIG. 14 illustrates similar changes in bipolar-sensed electrograms. FIG. 15 shows the influence of rejection on intrinsic, rather than stimulated, intracardiac electrograms. In all cases, the solid line denotes the normal waveform and the broken line designates the heart rejection waveform.

Referring back to FIG. 8, it is desirable to have a memory log of the time history for each metric. Data is pertinent to rejection diagnosis for about 30 days, so the device stores one value per day for each metric. In logging counter block 81, the device counts the number of data analysis operations since the last data logging. When one day has passed since the last daily metric data update, software stores the value of the short-term filter result for each metric in a circular memory buffer in daily metric update block 82. In a circular memory buffer, the newest data entry replaces the oldest.

At the end of the procedure of FIG. 8, the device enters a wait state 83. When the internal timer requests a new measurement, the procedure begins again in stimulation pulse block 70.

This data is accessed on a telemetric command by an external programmer. In response to a command, the device telemeters the requested data to the programmer. The programmer either displays this data or informs the patient to consult with the physician if the results are abnormal.

Referring back to FIG. 3, upon completion of the various procedures 51 to 57, the end signature 58 subprocedure provides notification to anyone monitoring the cardiac signal that the FIG. 3 operation is ending. The start (50) and end (58) signature operations are the same except for possible differences in the stimulus pulse amplitude. A successful vario 54 operation will have set the stimulation amplitude to the stimulation threshold plus margin value. A procedure failure such as too large a stimulus threshold value, or failure of the residual artifact test, results in a safe default stimulation amplitude. Following the end signature 58 sub-procedure, the device 1 enters the wait state 59 to await one of the events which restarts the start signature 50 sub-procedure.

Figure 16:
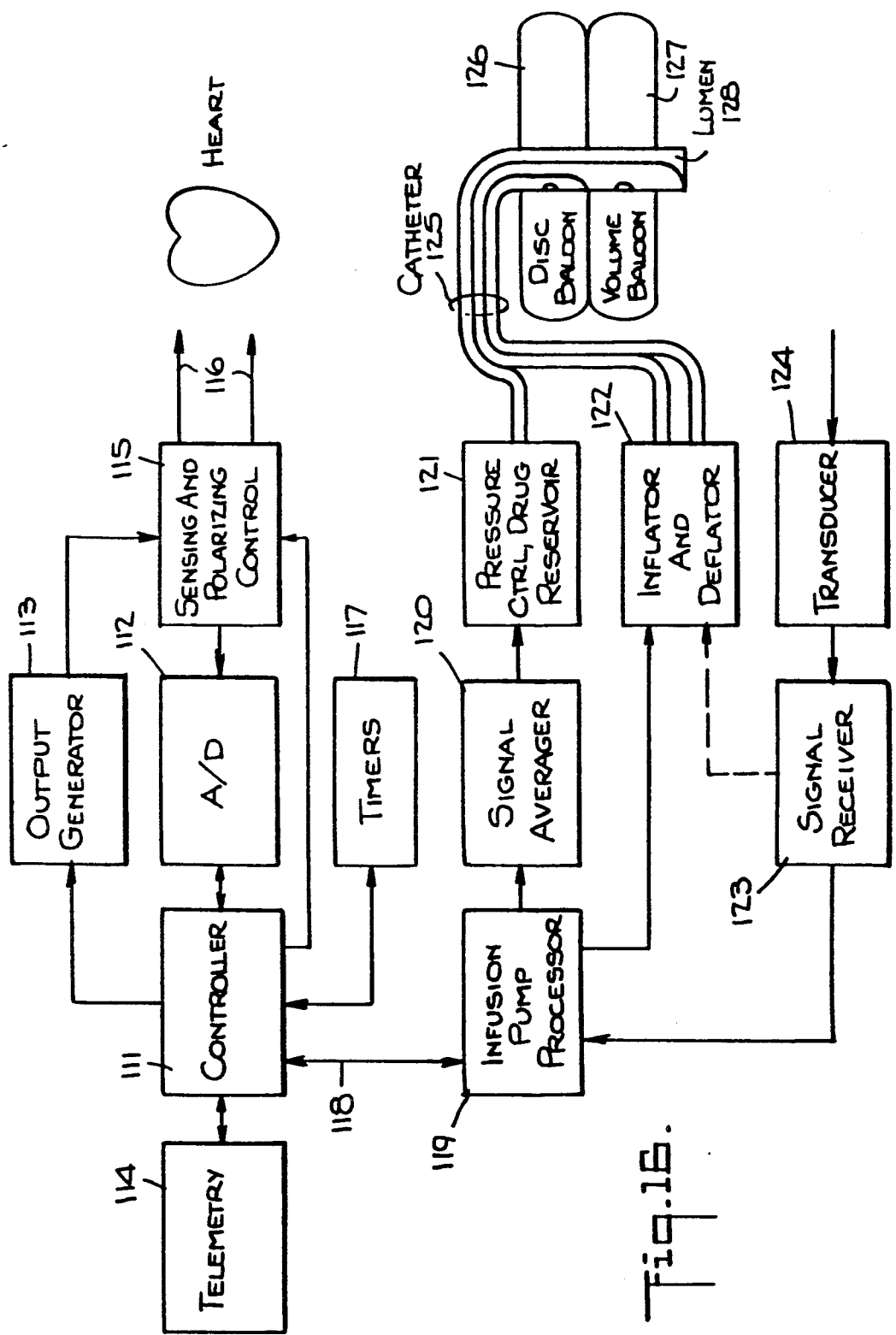
FIG. 16 is a block diagram of an illustrative embodiment of the invention in the form of an implanted drug infusion pump controller.

The block diagram of FIG. 16 illustrates one embodiment of the invention, in which an automatic control system is employed for analyzing the time history of stimulated intracardiac electrogram signals stored within the apparatus, calculating a desired dosage using a predetermined relationship between the signals and drug requirements, and controlling the output of a drug infusion pump accordingly. The implanted drug infusion pump controller combines the elements of the allograft rejection monitor and an infusion pump using standard data communication connections and additional control software within the controller of the allograft rejection monitoring apparatus. One such controllable infusion pump is described in the aforesaid U.S. Pat. No. 4,531,936, entitled "Device and Method for the Selective Delivery of Drugs to the Myocardium". The objective of the allograft rejection monitoring apparatus shown in FIG. 1 is to derive an allograft rejection control parameter indicative of transplant rejection. (Blocks 111 to 117 in FIG. 16 perform the same functions and operate in the same manner as blocks 11 to 17 in FIG. 1.) The implanted drug infusion pump controller software derives the allograft rejection control parameter in the same manner, uses it to determine timed control signals, and communicates these signals over the interprocessor communication lines 118 to the infusion pump processor 119. In addition to such signals derived from the allograft control parameter, controller software also sends signals over the interprocessor communication lines 118 which indicate the time of occurrence of stimulated and natural cardiac events. The infusion pump processor 119 uses information concerning the timing of cardiac events in conjunction with blood pressure information from a transducer 124 (by way of a signal receiver 123) to control the timing of signals to a pressure controller and drug reservoir block 121 (by way of a signal averager 120) and a balloon deflator and inflator 122. The blood pressure transducer 124 is implanted within the patient's circulatory system in a location which allows proper surveillance of systolic and diastolic pressure. The signal receiver 123 conditions the signal from the transducer 124 to provide digital codes indicating the timing and amplitude of these pressures. The infusion pump processor 119 synchronizes the timing of control signals to the pressure controller and drug reservoir block 121 and to the balloon deflator and inflator 122 according to the blood pressure and cardiac event information. The signal averager 120 conditions the digital control signals from the infusion pump processor 119 into an analog form, for usage by the pressure controller and drug reservoir block 121. A balloon catheter 125, which is implanted into a patient's ascending aorta, delivers drugs to the circulatory system. The catheter 125 has several lumens. At its proximal port, lumen 128 is fed by the drug reservoir within the pressure controller and drug reservoir block 121 for the injection of drugs or therapeutic agents. The distal end of lumen 128 is open to allow drug infusion into the circulatory system. The distal portion of the catheter includes the balloon apparatus made up of a disc balloon lumen 126, for occluding the aorta at an appropriate time, and a volume balloon lumen 127, for assisting in the delivery of the drug. The infusion pump processor 119 sends signals to the balloon deflator and inflator 122 to control the timing and intensity of inflation of lumens 126 and 127. The balloon deflator and inflator 122 inflates the disc balloon lumen 126 to obstruct the aorta during diastole. Then the pressure controller and drug reservoir block 121 injects the drug by way of lumen 128 and the balloon deflator and inflator 122 inflates the volume balloon 127, forcing the drug directly into the circulatory system.

Figure 17:
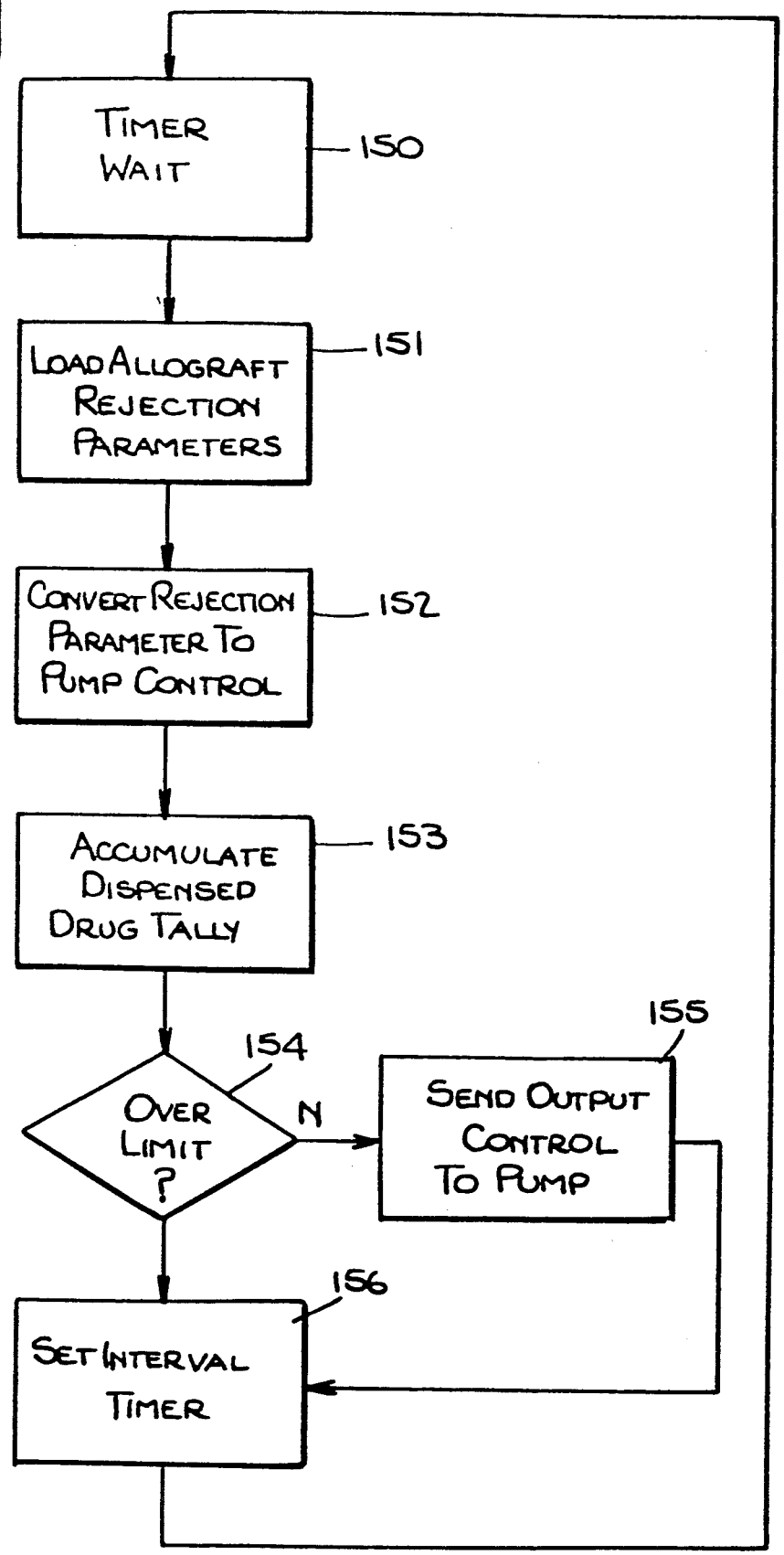
FIG. 17 is a flow chart illustrating the operational steps of the infusion pump control parameter derivation performed by the embodiment of the invention of FIG. 16.

Referring to FIG. 17, the infusion pump control signal procedure is normally idling in wait state 150. The timer (block 17 of FIG. 1) activates this software procedure following a predetermined time interval since the last activation. Upon receiving the timer wake-up, software loads, in block 151, the allograft rejection control parameter most recently derived in connection with block 80 of FIG. 8. The short and long-term filtering operations performed when deriving this parameter provide immunity from transient variations, including circadian rhythms. In block 152, software maps the allograft rejection control parameter into a pre-established table of values which determine the immunosuppression agent dosage. A physician determines the flow rate of the drug for any value of the allograft rejection control parameter and sets the values within the table accordingly, using the communication capabilities of the device. For each value of the parameter, the table determines the control rate by specifying both an amount of agent delivered upon a timer wakeup and an interval between wakeups. In block 153, software accumulates the amount of drug dispensed in a preset interval (for example, a day) by subtracting the oldest dosage sample stored in a circular memory from an accumulator, adding the current dosage sample into the accumulator, and then replacing the oldest dosage sample in the circular memory with the current dosage sample. In block 154, software prevents the amount of drug dispensed in the preset interval to exceed a limit value set by a physician using an external communicating device. If the accumulated dosage does not exceed the limit, in block 155 software writes a code to the infusion pump processor 119 of FIG. 16 indicating the number of drops of drug to deliver and activating the function of the pump as previously described. In block 156, software resets the interval until the next timer wakeup to the value determined in block 152.

Although the invention is described with reference to particular embodiments, it is to be understood that such embodiments are merely illustrative of the application of the principles of the invention. Numerous modifications may be made therein and other arrangements may be devised without departing from the spirit and scope of the invention.

We claim:

1. A cardiac allograft rejection monitor adapted to be implanted in a patient, comprising:
    means for generating cardiac stimulation pulses,
    means for sensing a stimulated cardiac depolarization signal in response to the generation of a cardiac stimulation pulse,
    means for periodically ascertaining the value of a measured allograft rejection control parameter which is based on an analysis of the sensed stimulated cardiac depolarization signal,
    means for detecting changes in the measured allograft rejection control parameter over time which are indicative of the occurrence of allograft rejection, and
    means for storing information indicative of the occurrence of allograft rejection and for communicating said information to an external device.

2. A cardiac allograft rejection monitor in accordance with claim 1, further comprising:
    means for determining whether the generation of a cardiac stimulation pulse successfully stimulates a response from the heart,
    means for temporarily suspending the operation of said ascertaining means for any cardiac cycle wherein the cardiac stimulation pulse fails to stimulate a response from the heart, and
    means for increasing the amplitude of the cardiac stimulation pulse when the cardiac stimulation pulse fails to stimulate a response from the heart over a plurality of consecutive cardiac cycles.

3. A cardiac allograft rejection monitor in accordance with claim 1, wherein said generated cardiac stimulation pulses each cause a corresponding stimulation polarization artifact to be initiated, and further comprising:
    means for minimizing the stimulation polarization artifact that is initiated by the generation of a cardiac stimulation pulse.

4. A cardiac allograft rejection monitor in accordance with claim 3, further comprising:
    means for determining when said minimizing means is incapable of minimizing the stimulation polarization artifact, and
    means for suspending the operation of said ascertaining means until said minimizing means becomes capable of minimizing the stimulation polarization artifact.

5. A cardiac allograft rejection monitor in accordance with claim 1, wherein said generated cardiac stimulation pulses each cause a corresponding stimulation polarization artifact to be initiated, and further comprising:
    means for determining whether the generation of a cardiac stimulation pulse successfully stimulates a response from the heart,
    means for temporarily suspending the operation of said ascertaining means for any cardiac cycle wherein the cardiac stimulation pulse fails to stimulate a response from the heart,
    means for increasing the amplitude of the cardiac stimulation pulse when the cardiac stimulation pulse fails to stimulate a response from the heart over a plurality of consecutive cardiac cycles, and
    means for minimizing the stimulation polarization artifact that is initiated by the generation of a cardiac stimulation pulse.

6. A cardiac allograft rejection monitor in accordance with claim 5, further comprising:
    means for determining when said minimizing means is incapable of minimizing the stimulation polarization artifact, and
    means for suspending the operation of said ascertaining means until said minimizing means becomes capable of minimizing the stimulation polarization artifact.

7. A cardiac allograft rejection monitor in accordance with claim 1, further comprising:
    means for setting the sensitivity of said sensing means to a level preventing signal saturation while maximizing the stimulated cardiac depolarization signal.

8. A cardiac allograft rejection monitor in accordance with claim 1, wherein said generated cardiac stimulation pulses each cause a corresponding stimulation polarization artifact to be initiated, and further comprising:
    means for setting the sensitivity of said sensing means to a level preventing signal saturation while maximizing the stimulated cardiac depolarization signal,
    means for determining whether the generation of a cardiac stimulation pulse successfully stimulates a response from the heart,
    means for temporarily suspending the operation of said ascertaining means for any cardiac cycle wherein the cardiac stimulation pulse fails to stimulate a response from the heart,
    means for increasing the amplitude of the cardiac stimulation pulse when the cardiac stimulation pulse fails to stimulate a response from the heart over a plurality of consecutive cardiac cycles, and
    means for minimizing the stimulation polarization artifact that is initiated by the generation of a cardiac stimulation pulse.

9. A cardiac allograft rejection monitor in accordance with claim 8, wherein said means for periodically ascertaining the value of a measured allograft rejection control parameter further comprises:
   means for measuring the peak magnitude of the sensed stimulated cardiac depolarization signal,
   means for measuring the depolarization time duration from the onset to the end of the stimulated cardiac depolarization signal, and
   means for determining the ratio of said peak magnitude to said depolarization time duration.

10. A cardiac allograft rejection monitor in accordance with claim 8, wherein said means for periodically ascertaining the value of a measured allograft rejection control parameter further comprises:
   means for deriving the integrated area of the sensed stimulated cardiac depolarization signal.

11. A cardiac allograft rejection monitor in accordance with claim 8, wherein said sensing means further senses a repolarization signal in response to the generation of a cardiac stimulation pulse, wherein said means for periodically ascertaining the value of a measured allograft rejection control parameter is further based on an analysis of said sensed stimulated cardiac repolarization signal, and wherein said ascertaining means further comprises:
   means for deriving the integrated area of the combined sensed stimulated cardiac depolarization signal and sensed stimulated cardiac repolarization signal.

12. A cardiac allograft rejection monitor in accordance with claim 1, wherein said means for periodically ascertaining the value of a measured allograft rejection control parameter further comprises:
   means for measuring the peak magnitude of the sensed stimulated cardiac depolarization signal,
   means for measuring the depolarization time duration from the onset to the end of the stimulated cardiac depolarization signal, and
   means for determining the ratio of said peak magnitude to said depolarization time duration.

13. A cardiac allograft rejection monitor in accordance with claim 1, wherein said means for periodically ascertaining the value of a measured allograft rejection control parameter further comprises:
   means for deriving the integrated area of the sensed stimulated cardiac depolarization signal.

14. A cardiac allograft rejection monitor in accordance with claim 1, wherein said sensing means further senses a repolarization signal in response to the generation of a cardiac stimulation pulse, wherein said means for periodically ascertaining the value of a measured allograft rejection control parameter is further based on an analysis of said sensed stimulated cardiac repolarization signal, and wherein said ascertaining means further comprises:
   means for deriving the integrated area of the combined sensed stimulated cardiac depolarization signal and sensed stimulated cardiac repolarization signal.

15. A cardiac allograft rejection monitor in accordance with claim 1, for controlling the output of an implantable drug infusion pump, further comprising:
   means for deriving an infusion pump control parameter from changes in the measured allograft rejection control parameter over time, and
   means for controlling said implantable drug infusion pump based on a time value of the infusion pump control parameter.

16. A cardiac allograft rejection monitor in accordance with claim 15, wherein said generated cardiac stimulation pulses each cause a corresponding stimulation polarization artifact to be initiated, and further comprising:
   means for setting the sensitivity of said sensing means to a level preventing signal saturation while maximizing the stimulated cardiac depolarization signal,
   means for determining whether the generation of a cardiac stimulation pulse successfully stimulates a response from the heart,
   means for temporarily suspending the operation of said ascertaining means for any cardiac cycle wherein the cardiac stimulation pulse fails to stimulate a response from the heart,
   means for increasing the amplitude of the cardiac stimulation pulse when the cardiac stimulation pulse fails to stimulate a response from the heart over a plurality of consecutive cardiac cycles, and
   means for minimizing the stimulation polarization artifact that is initiated by the generation of a cardiac stimulation pulse.

17. A cardiac allograft rejection monitor in accordance with claim 16, wherein said means for periodically ascertaining the value of a measured allograft rejection control parameter further comprises:
   means for measuring the peak magnitude of the sensed stimulated cardiac depolarization signal,
   means for measuring the depolarization time duration from the onset to the end of the stimulated cardiac depolarization signal, and
   means for determining the ratio of said peak magnitude to said depolarization time duration.

18. A cardiac allograft rejection monitor in accordance with claim 16, wherein said means for periodically ascertaining the value of a measured allograft rejection control parameter further comprises:
   means for deriving the integrated area of the sensed stimulated cardiac depolarization signal.

19. A cardiac allograft rejection monitor in accordance with claim 16, wherein said sensing means further senses a re-polarization signal in response to the generation of a cardiac stimulation pulse, wherein said means for periodically ascertaining the value of a measured allograft rejection control parameter is further based on an analysis of said sensed stimulated cardiac repolarization signal, and wherein said ascertaining means further comprises:
   means for deriving the integrated area of the combined sensed stimulated cardiac depolarization signal and sensed stimulated cardiac repolarization signal.

20. A method of monitoring cardiac allograft rejection from leads implanted in a patient's heart, comprising the steps of:
   generating cardiac stimulation pulses,
   sensing a stimulated cardiac depolarization signal in response to the generated cardiac stimulation pulse,
   periodically ascertaining the value of a measured allograft rejection control parameter which is based on an analysis of the sensed stimulated cardiac depolarization signal, detecting changes in the measured allograft rejection control parameter over time which are indicative of the occurrence of allograft rejection, and storing information indicative of the occurrence of allograft rejection and communicating the information to an external device.

21. A method of monitoring cardiac allograft rejection in accordance with claim 20, wherein said generated cardiac stimulation pulses each cause a corresponding stimulation polarization artifact to be initiated, and further comprising the steps of:

setting the sensitivity of said sensing step to a level preventing signal saturation while maximizing the stimulated cardiac depolarization signal, determining whether the generation of a cardiac stimulation pulse successfully stimulates a response from the heart, temporarily suspending the operation of said ascertaining step when cardiac stimulation pulses fail to stimulate responses from the heart, increasing the amplitude of cardiac stimulation pulses when the cardiac stimulation pulses fail to stimulate a response from the heart over a plurality of consecutive cardiac cycles, and minimizing the stimulation polarization artifact that is initiated by the generation of cardiac stimulation pulses.

22. A method of monitoring cardiac allograft rejection in accordance with claim 21, wherein said step of periodically ascertaining the value of a measured allograft rejection control parameter further comprises the sub-steps of:

measuring the peak magnitude of the sensed stimulated cardiac depolarization signal, measuring the depolarization time duration from the onset to the end of the stimulated cardiac depolarization signal, and determining the ratio of said peak magnitude to said depolarization time duration.

23. A method of monitoring cardiac allograft rejection in accordance with claim 21, wherein said step of periodically ascertaining the value of a measured allograft rejection control parameter further comprises the sub-step of:

deriving the integrated area of the sensed stimulated cardiac depolarization signal.

24. A method of monitoring cardiac allograft rejection in accordance with claim 21, wherein during said sensing step a stimulated repolarization signal is also sensed in response to the generated cardiac stimulation pulse, wherein said step of periodically ascertaining the value of a measured allograft rejection control parameter is further based on an analysis of said sensed stimulated cardiac repolarization signal, and wherein said ascertaining step further comprises the sub-step of:

deriving the integrated area of the combined sensed stimulated cardiac depolarization signal and sensed stimulated cardiac repolarization signal.

* * * * *